US010703713B2

(12) United States Patent
Loddenkemper et al.

(10) Patent No.: US 10,703,713 B2
(45) Date of Patent: Jul. 7, 2020

(54) PROCESS FOR PREPARING AN ISOCYANATE

(71) Applicant: COVESTRO DEUTSCHLAND AG, Leverkusen (DE)

(72) Inventors: Tim Loddenkemper, Dormagen (DE); Jurgen Arras, Itzehoe (DE); Markus Dugal, Kempen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/469,426

(22) PCT Filed: Dec. 18, 2017

(86) PCT No.: PCT/EP2017/083379
§ 371 (c)(1),
(2) Date: Jun. 13, 2019

(87) PCT Pub. No.: WO2018/114846
PCT Pub. Date: Jun. 28, 2018

(65) Prior Publication Data
US 2020/0095194 A1 Mar. 26, 2020

(30) Foreign Application Priority Data

Dec. 21, 2016 (EP) .................................... 16205620

(51) Int. Cl.
*C07C 263/20* (2006.01)
*B01D 3/14* (2006.01)

(52) U.S. Cl.
CPC ............ *C07C 263/20* (2013.01); *B01D 3/141* (2013.01)

(58) Field of Classification Search
CPC ...... C07C 263/10; C07C 263/20; B01D 3/141
USPC ........................................................ 560/347
See application file for complete search history.

(56) References Cited

U.S. PATENT DOCUMENTS

| | | | |
|---|---|---|---|
| 2,884,360 A | 4/1959 | Bloom et al. | |
| 2,884,362 A | 4/1959 | Bloom et al. | |
| 3,128,310 A | 4/1964 | Koch | |
| 3,331,876 A | 7/1967 | Van Horn et al. | |
| 3,694,323 A | 9/1972 | Cooper et al. | |
| 3,713,833 A | 1/1973 | Lindholm et al. | |
| 3,987,075 A | 10/1976 | Schnabel | |
| 4,289,589 A | 9/1981 | Koehler et al. | |
| 4,289,732 A | 9/1981 | Bauer et al. | |
| 4,372,891 A | 2/1983 | Hilbert et al. | |
| 4,419,295 A | 12/1983 | Hennig et al. | |
| 4,847,408 A | 7/1989 | Frosch et al. | |
| 4,851,570 A | 7/1989 | Zaby et al. | |
| 4,851,571 A | 7/1989 | Sauer et al. | |
| 4,915,509 A | 4/1990 | Sauer et al. | |
| 4,918,220 A * | 4/1990 | Collas ................... C07C 263/20 560/352 |
| 5,117,048 A | 5/1992 | Zaby et al. | |
| 5,202,358 A | 4/1993 | Scholl et al. | |
| 5,314,588 A | 5/1994 | Zarnack et al. | |
| 5,354,432 A | 10/1994 | Arribas et al. | |
| 5,424,386 A | 6/1995 | Gebauer et al. | |
| 5,446,196 A | 8/1995 | Benedix et al. | |
| 5,449,818 A | 9/1995 | Biskup et al. | |
| 5,902,459 A | 5/1999 | Gagnon et al. | |
| 5,931,579 A | 8/1999 | Gallus et al. | |
| 6,120,699 A | 9/2000 | Narayan et al. | |
| 6,307,096 B1 | 10/2001 | Sommer et al. | |
| 8,692,016 B2 | 4/2014 | Sanders et al. | |
| 2003/0114705 A1 | 6/2003 | Friedrich et al. | |
| 2003/0216597 A1 | 11/2003 | Jenne et al. | |
| 2003/0230476 A1 | 12/2003 | Brady et al. | |
| 2004/0068137 A1 | 4/2004 | Herold et al. | |
| 2004/0118672 A1 | 6/2004 | Grun et al. | |
| 2004/0167354 A1 | 8/2004 | Biskup et al. | |
| 2005/0113601 A1 | 5/2005 | Herold et al. | |
| 2005/0137417 A1 | 6/2005 | Meyn et al. | |
| 2006/0011463 A1 | 1/2006 | Sohn et al. | |

(Continued)

FOREIGN PATENT DOCUMENTS

DE 2703313 A1 8/1978
DE 288599 A5 4/1991
(Continued)

OTHER PUBLICATIONS

Wegener, G. et al., Trends in industrial catalysis in the polyurethane industry, Applied Catalysis A: General, 2001, vol. 221, p. 303-335, Elsevier Science B.V. (abstract).

(Continued)

*Primary Examiner* — Yong L Chu
(74) *Attorney, Agent, or Firm* — Donald R. Palladino

(57) ABSTRACT

The industrial scale preparation of isocyanates gives rise to distillation bottom streams that are in need of further workup. These distillation bottom streams still also contain, as well as a distillation residue consisting of compounds that can be evaporated without decomposition only with great difficulty if at all (also referred to as residue for short), proportions of the desired target product (i.e. isocyanate to be prepared). The present invention relates to a process that enables recovery, in an efficient manner, of this proportion of isocyanate to be prepared in a distillation bottom stream which is obtained in the workup of the crude liquid process product which contains the isocyanate to be prepared and is formed in an isocyanate preparation process. More particularly, the present invention relates to a drying step in which the isocyanate to be prepared is recovered to form a solid material that has been largely to completely freed of this isocyanate. This drying step is characterized by a minimum content of compounds containing carbodiimide groups of 15% by mass, preferably 20% by mass, more preferably 30% by mass, based on the total mass of the distillation residue fed to the drying apparatus used, where this minimum content can also be adjusted by an in situ carbodiimidization.

23 Claims, 4 Drawing Sheets

(56) References Cited

U.S. PATENT DOCUMENTS

| | | |
|---|---|---|
| 2006/0089507 A1 | 4/2006 | Sohn et al. |
| 2006/0183946 A1 | 8/2006 | Zechlin et al. |
| 2006/0223966 A1 | 10/2006 | Brodhagen et al. |
| 2007/0015934 A1 | 1/2007 | Wolfert et al. |
| 2007/0265465 A1 | 11/2007 | Keggenhoff et al. |
| 2007/0299279 A1 | 12/2007 | Pohl et al. |
| 2008/0167490 A1 | 7/2008 | Pohl et al. |
| 2010/0160673 A1 | 6/2010 | Bruns et al. |
| 2011/0021811 A1 | 1/2011 | Lorenz et al. |
| 2015/0126769 A1 | 5/2015 | Steffens et al. |

FOREIGN PATENT DOCUMENTS

| | | |
|---|---|---|
| DE | 4104305 A1 | 8/1992 |
| GB | 795639 A | 5/1958 |
| GB | 1238669 A | 9/1968 |

OTHER PUBLICATIONS

Ullmann's Encyclopedia of Industrial Chemistry, 1991, p. 390 ff, vol. A19, 5th ed., VCH Verlagsgesellschaft mbH, Weinheim.

Verlag, Carl-Hanser, Polyurethane Handbook, 1993, 2nd ed., p. 60 ff, G. Oertel (ed.).

PERP Report for TDI/MDI, Chem Systems, Process Evaluation Research Planning TDI/MDI 99/98 S8, Chem Systems, 1999, p. 27-32, Tarrytown, NY.

International Search Report—PCT/EP2017/083379—dated Mar. 26, 2018; Megido, Benigno.

\* cited by examiner

PROCESS FOR PREPARING AN ISOCYANATE

CROSS-REFERENCE TO RELATED APPLICATION

This application is a national stage application under 35 U.S.C. § 371 of PCT/EP2017/083379, filed Dec. 18, 2017, which claims the benefit of European Application No. 16205620.4, filed Dec. 21, 2016, both of which are incorporated by reference herein.

The industrial scale preparation of isocyanates affords distillation bottom streams that are in need of further workup. These distillation bottom streams contain not only a distillation residue consisting of compounds evaporable without decomposition only with great difficulty, if at all (also referred to as residue for short), but also proportions of the desired target product (i.e. the isocyanate to be prepared). The present invention relates to a process that enables recovery, in an efficient manner, of this proportion of isocyanate to be prepared in a distillation bottom stream obtained in the workup of the crude liquid process product containing the isocyanate to be prepared which is formed in an isocyanate preparation process. More particularly, the present invention relates to a drying step in which the isocyanate to be prepared is recovered to form a solid that has been freed largely to completely of this isocyanate. This drying step is characterized by a minimum content of compounds containing carbodiimide groups of 15% by mass, preferably 20% by mass, more preferably 30% by mass, based on the total mass of the distillation residue supplied to the drying apparatus used, where this minimum content can also be adjusted by in situ carbodiimidization.

BACKGROUND

The prior art for treatment of distillation bottom streams from isocyanate preparation that comprise the distillation residues mentioned describes various processes. General aims of what is called "residue treatment" are the maximization of the isocyanate yield, the minimization of the amount of residue obtained that has been largely to entirely freed of isocyanate, operationally reliable configuration of the residue treatment and the best possible inexpensive and simple utilization of the residue volume no longer utilizable for the isocyanate preparation process.

The following processes are known in principle:

In principle, a distillate bottom stream comprising the distillation residue can be combusted continuously or batchwise. The process is technically simple and can be used to raise useful steam if a plant for thermal utilization which is suitable for the purpose exists in the vicinity of the isocyanate production plant, in order to assure disposal via a pipeline connection. However, the great disadvantage of this process is the loss of yield, caused by the fact that the distillation bottom stream comprising the distillation residue always also contains proportions of the isocyanate product of value which is burnt as well. If the distillation of the isocyanate were to be conducted in such a way that the isocyanate were to be removed completely or virtually completely from the distillation bottoms, what would remain would be a solid distillation bottoms phase that could be processed only with great difficulty and consisted almost exclusively of residue. In order to avoid this, distillation conditions are typically chosen such that the bottom product from the distillation column remains liquid, but this is only possible if it still contains a substantial proportion of the isocyanate to be prepared, which is thus inevitably sent to the combustion as well.

To minimize the isocyanate yield losses, the distillation bottom stream can be transferred into a stirred and heated vessel and mixed with high-boiling hydrocarbons, preferably bitumen, that are inert under the distillation conditions to distill off a maximum amount of the free isocyanate still present in the residue (EP 0 548 685 A2). The remaining residue that has been largely freed of isocyanate can be discharged as a free-flowing solid and sent to incineration. Disadvantages of this process include not only the use of a substance foreign to the process (bitumen) but also yield losses through polymerization of the isocyanate since the process includes high residence times at high temperature.

A further process for residue treatment, described in EP 0 626 368 A1, is characterized by the use of heated, product-agitating vacuum driers with a horizontal shaft. The use of bitumen, for example, has the effect that, as in the above-mentioned example of the process according to EP 0 548 685 A2, the remaining residue is obtained as a free-flowing solid that can be used as a fuel in cement works for example. The advantage of this process over that mentioned above is an increase in yield. However, the use of mechanical moving parts harbors the risk of elevated wear and associated maintenance expenditure. This is especially true when the residue to be worked up has a very high viscosity. The use of drying apparatuses of this kind with mechanical moving parts, even though it is basically tried and tested, is therefore not always free of challenges in everyday operation. The present invention is concerned with such challenges inter alia.

The patent literature also describes processes in which isocyanate distillation bottom streams comprising distillation residues are chemically converted in order to obtain industrially utilizable materials of value, for example the reaction of a distillation bottom stream comprising residue from the preparation of tolylene diisocyanate with alkanolamine (U.S. Pat. No. 5,902,459) or with isocyanates of the diphenylmethane series (DE 42 11 774 A1, U.S. Pat. No. 3,694,323).

The hydrolysis of isocyanate distillation bottom streams with water to achieve recovery of the starting amine, especially in the preparation of tolylene diisocyanate (TDI hereinafter), is a field that has been worked on for some long time already and is described in U.S. Pat. Nos. 3,128,310, 3,331,876, GB 795,639, DE 27 03 313 A1 and EP 1 935 877 A1 for example. What is unsatisfactory in these processes is that a portion of the isocyanate product of value has to be hydrolyzed back to the starting material and phosgenated again. This does send the isocyanate present in the distillation bottom stream to a viable physical use, but it would be desirable to be able to recover the isocyanate as such from the distillation bottom streams.

EP 1 413 571 A1 and EP 1 371 633 A1 are concerned with the optimization of the workup of TDI by using a dividing-wall column in the distillation which results, inter alia, in a reduction in the TDI content in the bottom product. But here too, it is not possible to completely prevent an isocyanate-containing distillation bottom stream from being obtained.

EP 0 017 972 A1 describes a process for separating TDI and/or higher-boiling solvents from distillation bottom streams that arise in the preparation of TDI by phosgenation of tolylenediamine by evaporative concentration in a fluidized bed at temperatures of 140 to 280° C. In this process, the droplets of the distillation bottom stream that have been introduced into the fluidized bed vessel by means of the introduction device are sprayed onto the surface of the initially charged particles, where they spread, which leads to evaporation of the product of value (TDI and/or solvent) and to formation of dish-shaped pellets of residue that are free of material of value. Such a granulation process generally does not have cycle times of any great length and has to be run down for the purpose of intermediate cleaning after particular time intervals. This is disadvantageous for the present case of workup of isocyanate-containing distillation bottom streams owing to the required inertization of the reaction space and the high temperatures, and the running-up problems.

WO 2014/009342 A1 is concerned with a spray drying process for obtaining monomeric isocyanate (i.e. the isocyanate to be prepared, which is desired as the target product, as opposed to unwanted high molecular weight polymers containing isocyanate groups) from distillation residue-containing bottom streams. The spray drying described affords a dried residue that has been largely to completely freed of monomeric isocyanate and a stream comprising monomeric isocyanate. Performance of this process requires a special reactor, and so it generally cannot be integrated into an existing isocyanate production plant without major refitting.

Further improvements in the field of workup of isocyanate distillation bottom streams comprising not only distillation residues but also proportions of the isocyanate to be prepared are therefore desirable. More particularly, it would be desirable to separate the desired target product, i.e. the isocyanate to be prepared, from the distillation bottom stream in a simple, operationally stable and economic manner in order to minimize yield losses and maintenance expenditure in continuous operation on the industrial scale as well, specifically also when the composition of the distillation bottom stream containing the residue is subject to production-related variations. It would also be desirable if such an improved process could be integrated in a simple manner into an already existing process that uses prior art drying apparatus (e.g. the heated, product-agitating vacuum driers with a horizontal shaft that have been mentioned).

SUMMARY

Taking account of the above, the present invention relates to the workup of a distillation bottom stream consisting of
  the isocyanate to be prepared,
  optionally low boilers (especially solvent) and
  distillation residue,
wherein said distillation bottom stream comes from the workup of a liquid crude process product which comprises the isocyanate to be prepared and is obtained by phosgenating the primary amine corresponding to the isocyanate to be prepared, wherein the workup of the distillation bottom stream comprises the following steps:
1) optionally pre-concentrating the distillation bottom stream in an evaporator by partially evaporating the isocyanate to be prepared which is present in the distillation bottom stream to obtain a pre-concentrated liquid stream depleted of isocyanate to be prepared;
2) drying the distillation bottom stream or the pre-concentrated liquid stream depleted of isocyanate to be prepared which has been obtained in step 1) in a drying apparatus at a temperature in the range from 150° C. to 500° C., preferably in the range from 185° C. to 300° C., more preferably in the range from 200° C. to 270° C., with evaporation and recovery of isocyanate to be prepared to form a solid process product, where the proportion by mass of compounds containing carbodiimide groups based on the total mass of the distillation residue supplied to the drying apparatus is adjusted to a value of at least 15%, preferably at least 20%, more preferably at least 30%.

Completely surprisingly, it has been found that the procedure of the invention of establishing a minimum content of compounds containing carbodiimide groups in drying step 2) can reduce or even prevent increased mechanical stress from the drying apparatus (e.g. rise in torque in drying apparatuses with a shaft) which is associated—as a result of the unavoidable rise in viscosity—with the thorough drying of the distillation residue, and this has a positive effect on the operational stability of the drying apparatus and hence on the operational stability of the overall process.

BRIEF DESCRIPTION OF THE DRAWINGS

Various features and characteristics of the inventions described in this specification may be better understood by reference to the accompanying figures, in which.

DETAILED DESCRIPTION

Figure 1:
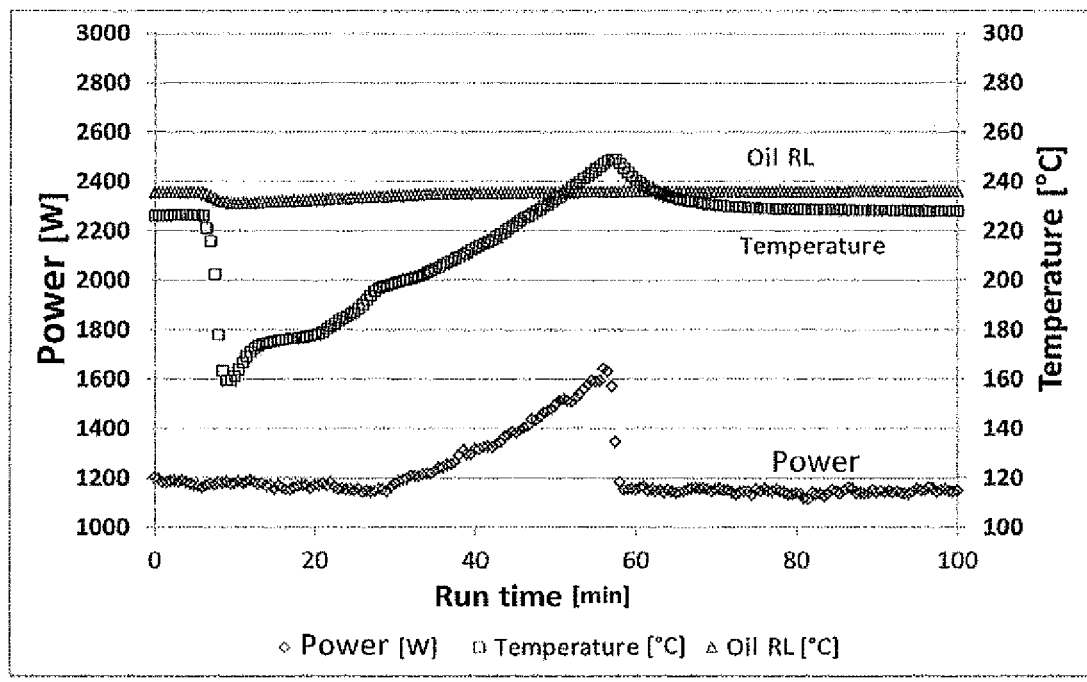
FIG. 1 is a graph illustrating the progression of the experiment of Example 1.

More particularly, the present invention provides a process for preparing an isocyanate, comprising the following steps:
  a) phosgenating the primary amine corresponding to the isocyanate to be prepared to obtain a liquid crude process product comprising the isocyanate to be prepared and a hydrogen chloride-comprising gaseous crude process product, with optional use of a solvent;
  b) working up the liquid crude process product obtained in step a), comprising the steps of:
  b.1) optionally separating dissolved phosgene and dissolved hydrogen chloride from the liquid crude process product obtained in step a) to obtain a phosgene- and hydrogen chloride-depleted liquid process product;
  b.2) optionally separating solvent from the liquid crude process product obtained in step a) or from the phosgene- and hydrogen chloride-depleted liquid process product obtained in step b) to obtain a phosgene-, hydrogen chloride- and solvent-depleted liquid process product;
  b.3) distilling the liquid crude process product obtained in step a) or the phosgene- and hydrogen chloride-depleted liquid process product obtained in step b.1) or the phosgene-, hydrogen chloride- and solvent-depleted liquid process product obtained in step b.2) to obtain a distillate stream comprising a first portion of the isocyanate to be prepared and a distillate bottom stream consisting of distillation residue, a second portion of the isocyanate to be prepared and optionally low boilers, especially solvent;

c) working up the distillation bottom stream obtained in step b.3), comprising the steps of:

c.1) optionally pre-concentrating the distillation bottom stream obtained in step b) in an evaporator by partially evaporating the second portion of the isocyanate to be prepared which is present in the distillation bottom stream obtained in step b) to obtain a pre-concentrated liquid stream depleted of isocyanate to be prepared;

c.2) drying the distillation bottom stream obtained in step b) or the pre-concentrated liquid stream depleted of isocyanate to be prepared which has been obtained in step c.1) in a drying apparatus at a temperature in the range from 150° C. to 500° C., preferably in the range from 185° C. to 300° C., more preferably in the range from 200° C. to 270° C., with evaporation and recovery of isocyanate to be prepared to form a solid process product, where the proportion by mass of compounds containing carbodiimide groups based on the total mass of the distillation residue supplied to the drying apparatus is adjusted to a value of at least 15%, preferably at least 20%, more preferably at least 30%.

Step c) of the process for preparing an isocyanate corresponds here to the above-described workup of a distillation bottom stream, and steps c.1) and c.2) of the process for preparing an isocyanate correspond to steps 1) and 2) of said workup of a distillation bottom stream. In addition, step b) of the process for preparing an isocyanate corresponds to the workup of the liquid crude process product which comprises the isocyanate to be prepared and is obtained by phosgenating the primary amine corresponding to the isocyanate to be prepared, from which the distillation bottom stream originates.

The invention is elucidated more particularly hereinafter with reference to the overall process comprising steps a) to c). This is done for the sake of simplicity and should not be understood such that these elucidations have an automatic limiting effect on the overall process.

In the context of the present invention, "primary amine corresponding to the isocyanate to be prepared" is considered to mean that amine that gives the isocyanate to be prepared on conversion of all $NH_2$ groups present to NCO groups.

According to the invention, the "distillation bottom stream" consists of at least the isocyanate to be prepared and the distillation residue defined hereinafter. In addition, the distillation bottom stream may also comprise the low boilers defined hereinafter. According to the invention, the distillation bottom stream accordingly consists of two constituents (isocyanate to be prepared and distillation residue) or three constituents (isocyanate to be prepared, low boilers and distillation residue).

In the context of the present invention, "distillation residue" is understood to mean that proportion of the distillation bottom stream obtained in the distillation from step b.3) that can be assigned neither to the isocyanate to be prepared nor—if any are present at all—to low boilers, "low boilers" being understood to mean all substances or azeotropically boiling mixtures of substances having a lower boiling point than the isocyanate to be prepared, or, if this isocyanate is in the form of an isomer mixture, lower than the lowest-boiling isomer of the isocyanate to be prepared (i.e., in the case of TDI, 2,6-TDI). Low boilers in this context are especially any solvent used from step a). Low boilers in the sense of low-boiling secondary components are generally either not present at all in the distillation bottom stream from step b.3) or are present at most in trace contents of up to 0.10% by mass, preferably up to 0.010% by mass, more preferably 0.0010% by mass, based on the total mass of the distillation bottom stream obtained in step b.3). The distillation residue contains compounds that do not evaporate under the pressure and temperature conditions chosen for step b.3) or that do not evaporate without decomposition at all. In order that the distillation bottom stream retains good processibility with regard to its flow properties (i.e. does not become too viscous or even firm), the isocyanate to be prepared is not distilled off completely in step b.3), and so a portion thereof remains in the distillation bottom stream. It is likewise possible not to completely distill off any solvent still present (from step a)) in step b.3), and to permit a residual solvent content in the distillation bottom stream of up to 10% by mass, preferably of up to 1.0% by mass, based on the total mass of the distillation bottom stream obtained in step b.3). The compounds in the distillation residue that are evaporable with difficulty, if at all—if they are not impurities from the primary amines used that run through the phosgenation process unchanged—are phosgenation products of high molecular weight, the structure of which is still not exactly known. For instance, they may be compounds that can be derived (in a formal sense) from polymerization products of the amine used by replacement of the unpolymerized amine groups by isocyanate groups. Phosgenation products of higher molecular weight may also partly form (by further reaction) in step b).

According to the invention, in this context, phosgenation products of higher molecular weight are also considered to mean "compounds containing carbodiimide groups" which likewise accumulate in the distillation bottom stream and should be considered as a constituent of the distillation residue in the terminology of the present invention. As is known to the person skilled in the art, carbodiimides are a substance group of organic compounds characterized by the structural feature R—N=C=N—R' where R and R' denote organic radicals. The phosgenation of primary amines can give rise to such compounds from the isocyanate to be prepared via elimination of carbon dioxide. In the case of a diamine, the simplest conceivable carbodiimide forms via the formation of an "—N=C=N—" bridge between two diisocyanate molecules. In this case, the two R and R' radicals in turn still contain free NCO functions. If these react further with isocyanate to be prepared or further carbodiimides having free NCO functions with elimination of $CO_2$, structures are formed with multiple "—N=C=N—" bridges and high molar masses.

The "proportion by mass of compounds containing carbodiimide groups based on the total mass of the distillation residue supplied to the drying apparatus" in step c.2) is thus formed by addition of up to three contributions, namely from (i) the mass of compounds containing carbodiimide groups present in the starting material from step c.2) (i.e. the distillation bottom stream obtained in step b) or the pre-concentrated liquid stream obtained in step c.1)), (ii) the mass of any added compounds containing carbodiimide groups and (iii) the mass of any compounds containing carbodiimide groups that are formed in situ in step c.2).

According to the invention, care should be taken that the sum total of (i), (ii) and (iii) divided by the total mass of the distillation residue supplied to the drying apparatus from step c.2) is at least 0.15, preferably at least 0.20, more preferably at least 0.30 (corresponding to at least 15% by mass, preferably at least 20% by mass, more preferably at least 30% by mass). In the case of a continuous process regime, the corresponding hourly mass flow rates form the basis.

It is sufficient when just one of the three components (i) to (iii) is non-zero and is sufficiently large that the requirements of the invention are fulfilled. It is possible, for example, to keep the proportion of compounds containing carbodiimide groups to be attributed to (i) and (iii) at zero (or close to zero) by suitable choice of process bonds (see further details further down), and to fulfill the requirements of the invention solely through addition of compounds containing carbodiimide groups from an external source. But it is also possible to dispense with such an external addition according to (ii) and to fulfill compliance with the requirements of the invention on the proportion by mass of compounds containing carbodiimide groups solely via the proportion according to (i) and/or (iii).

In principle, it is accordingly possible to distinguish between three cases that will be elucidated in more detail further down:

A. establishing process conditions that promote the formation of compounds containing carbodiimide groups in step a) and/or in step b) and/or—if conducted—in step c.1);
B. preparing compounds containing carbodiimide groups from the isocyanate to be prepared in a separate operation (e.g. by thermal or catalytically induced carbodiimidization of the isocyanate to be prepared) and supplying the compounds containing carbodiimide groups thus prepared to the drying apparatus from step c.2);
C. forming compounds containing carbodiimide groups in situ (for example by heating prior to the actual drying or performance of the drying at relatively high pressure) in step c.2).

Cases A, B and C can occur either individually or in conjunction with one another.

It is possible, in case A, to choose the process conditions in step a) and/or in step b) and/or—if conducted—in step c.1) such that the mass of compounds containing carbodiimide groups introduced into this step from step c.2) via the starting material is sufficiently great that the requirements of the invention on the minimum proportion by mass of containing carbodiimide groups in the distillation residue are fulfilled. In this case, external preparation or in situ preparation of compounds containing carbodiimide groups is then unnecessary.

It is likewise possible, in case B, to prepare compounds containing carbodiimide groups in a separate operation from the isocyanate to be prepared, and to supply them to step c.2), in such an amount that the requirements of the invention on the minimum proportion by mass of containing carbodiimide groups in the distillation residue are fulfilled. In this case, the establishment of process conditions according to case A or in situ preparation of compounds containing carbodiimide groups is then unnecessary.

It is likewise possible, in case C, to form the entire amount of compounds containing carbodiimide groups required to fulfill the requirements of the invention on the minimum proportion by mass of compounds containing carbodiimide groups in the distillation residue in situ in step c.2). In this case, the establishment of process conditions according to case A or external preparation of compounds containing carbodiimide groups is then unnecessary.

However, it is also possible to establish the proportion by mass of compounds containing carbodiimide groups based on the total mass of the distillation residue that is required in accordance with the invention by bringing about a combination of two or three of cases A, B and C mentioned.

Suitable process regimes for case A are elucidated in detail further down. To verify whether the conditions chosen for step a) and/or for step b) and/or—if conducted—for step c.1) are suitable, a determination of the proportion by mass of the compounds containing carbodiimide groups in the starting material to be dried from step c.2) is required. For this purpose, the person skilled in the art is familiar with various analytical methods, all of which can be employed in principle. A crucial factor for assessing whether the requirements of the invention on the minimum proportion by mass of compounds containing carbodiimide groups in the distillation residue are fulfilled, however, is the procedure outlined hereinafter ("Measurement methods I and II"):

First of all, the proportion by mass of compounds containing carbodiimide groups in the starting material to be dried which is sent to step c.2) is determined. This is accomplished by means of IR spectroscopy as outlined hereinafter ("Measurement method I").

Measurement Method I:

A sample of the starting material to be examined from step c.2) that has been cooled down to ambient temperature is dissolved in ortho-dichlorobenzene (ODB hereinafter) (the proportion by mass of the sample of the starting material from step c.2), based on the total mass of the solution in ODB to be prepared, is set here to 20%) and divided in a ratio of 1:1. A portion of the dissolved sample is boiled under reflux at ambient pressure for 15 min (heating temperature 190° C.) and then cooled indirectly in a water-ice bath. The boiling results in cleavage of uretonimine, the form in which carbodiimide is present at room temperature, back to carbodiimide and isocyanate. The other portion of the dissolved sample remains unchanged. The heat-treated sample is introduced into a cuvette (path length of the sample in the cuvette 150 to 200 µm) and placed into the measurement beam path of an IR spectrometer. The non-heat-treated solution is introduced into a cuvette with the same layer thickness as the measurement cuvette and placed into the comparative beam path of the IR spectrometer. An IR spectrum of the range from 2600 cm$^{-1}$ to 1900 cm$^{-1}$ is recorded. The extinction E at 2140 cm$^{-1}$ (height of the signal) is determined in relation to the baseline in the range from 2500 cm$^{-1}$ to 1900 cm$^{-1}$. The uretonimine content ω(UI) in % by mass (calculated for the molar mass M(UI) [in g/mol] of the uretonimine which is formed from the addition of one mole of the isocyanate to be prepared onto one mole of the carbodiimide formed by carbodiimidization of two moles of the isocyanate to be prepared) is calculated by the following equation:

$$\omega(UI)=[E(2140\ cm^{-1})\cdot M(UI)\cdot 100\%]/[d\cdot \varepsilon \cdot a].$$

where M(UI)=molar mass of the uretonimine as defined above in g/mol (478 in the case of TDI as the isocyanate to be prepared); d=path length of the sample in the cuvette in cm; ε=extinction coefficient in L/mol·cm; a=concentration of the solution analyzed in g/L.

Since 1 mol of the uretonimine is formed from 1 mol of the carbodiimide and one mole of the isocyanate be prepared, the proportion by mass of uretonimine thus ascertained can easily be converted to the proportion by mass of the carbodiimide ω(CD):

$$\omega(CD)=\omega(UI)\cdot M(CD)/M(UI);$$

where M(CD) corresponds for the molar mass in g/mol of the carbodiimide formed from 2 mol of the isocyanate to be prepared (304 in the case of TDI as isocyanate to be prepared).

The value for ω(CD) thus ascertained corresponds to the proportion by mass of compounds containing carbodiimide groups in the starting material supplied to step c.2). According to the invention, the reference parameter for the quantification of the proportion by mass of compounds containing carbodiimide groups is the total mass of the distillation residue supplied to the drying apparatus from step c.2). To determine the proportion by mass of compounds containing carbodiimide groups as thus defined, quantification of the proportion by mass of the distillation residue in the starting material supplied to step c.2) is required. The procedure for this purpose is as follows ("Measurement method II"):

Measurement Method II:

A weighed amount of a sample of the starting material to be supplied to step c.2) is initially charged in a laboratory distillation apparatus equipped with a droplet trap (Reitmayer distillation attachment) and distilled at a pressure of 1.0 mbar and at a heating temperature of 250° C. After 30 minutes (measured from the juncture at which pressure and temperature have attained the aforementioned target values), the heating is switched off and the apparatus is cooled down. The distillate obtained and the undistilled proportion of the sample remaining in the charge flask of the distillation apparatus are weighed. In the terminology of the present invention, the undistilled proportion of the sample is considered to be the distillation residue in the context of the invention. By comparison with the known mass of the sample initially charged in the distillation apparatus, the proportion by mass of distillation residue is determined quantitatively in the starting material to be supplied to step c.2). With this result and the result for ω(CD) from measurement method I, it is easily possible to calculate the proportion by mass of compounds containing carbodiimide groups based on the total mass of the distillation residue.

Once suitable conditions have been fixed in this way for step a) and/or for step b) and/or—if conducted—for step c.1), it is possible in principle to dispense with analysis of the starting material from step c.2) in continuous operation. However, it is advisable to conduct control tests to verify the result once ascertained from time to time, in continuous mode especially at least 1× every 720 h, preferably at least 1× every 360 h, more preferably at least 1× every 180 h, most preferably at least 1× every 90 h.

If case A applies and the process conditions in step a) and/or in step b) and/or—if conducted—in step c.1) are chosen such that the mass of compounds containing carbodiimide groups introduced into this step via the starting material from step c.2) is already sufficiently high to meet the requirements of the invention on the minimum proportion by mass of containing carbodiimide groups in the distillation residue, it is possible to dispense with any measurement of the proportion of compounds containing carbodiimide groups that originate from (iii) since it does not matter whether or not further compounds containing carbodiimide groups are formed in situ in step c.2) (no reduction in the proportion of compounds containing carbodiimide groups is to be expected chemically in step c.2)). In this case, any addition of compounds containing carbodiimide groups as per (ii) can of course also be dispensed with.

If this case does not apply, in accordance with the invention, it has to be ensured in some other way that compounds containing carbodiimide groups are present in a sufficient amount in step c.2).

In case B, this can be accomplished by adding compounds containing carbodiimide groups from an external source. The crucial proportion by mass of compounds containing carbodiimide groups in the added material from an external source is that determined by measurement method I. According to the amount of material added and the proportion by mass of compounds containing carbodiimide groups therein, it is clear even without quantification of the distillation residue whether the demands of the invention are fulfilled (namely when the minimum proportion by mass of compounds containing carbodiimide groups required in accordance with the invention, based on the total mass of the distillation residue, has been attained even assuming that the distillation bottoms consist entirely of residue). Should a quantification of the distillation residue be necessary, the determination by measurement method II is crucial.

It is likewise possible, via the choice of suitable process conditions, to ensure that compounds containing carbodiimide groups are formed in situ in step c.2). Suitable process regimes for this case C are elucidated in detail further down. To verify whether the conditions chosen for step c.2) are suitable for this purpose, the mass balance of the drying from step c.2) is monitored as follows ("measurement method III"):

Measurement Method III:

The drying apparatus from step c.2) is supplied with a starting material to be dried with a known proportion by mass (determined by measurement method II) of distillation residue. The distillate obtained by measurement method II in the distillation described consists of the isocyanate to be prepared and optionally low boilers (especially solvent originating from step a)). The composition of the distillate (ratio of low boilers to isocyanate to be prepared) is quantified by gas chromatography (HP-5, 30 m*320 µm*0.25 µm, 40-250° C., 1-20° C./min, TCD detector).

Column: Agilent 19091J-413: 1300.52926, HP-5, 5% phenyl methyl siloxane, 325° C.: 30 m×320 µm×0.25 µm.

Heating ramp: starting temperature 40° C., then 1° C./min to 45° C., then 20° C./min to 250° C., hold at 250° C. for 5 min.

Elution time: 20.25 min.

Detector: TCD (thermal conductivity detector).

In this way, it is ascertained how much isocyanate to be prepared can be distilled out of the starting material to be dried in step c.2). In step c.2), isocyanate to be prepared is evaporated to form a solid process product and recovered. The mass (the hourly mass flow rate in a continuous process regime) of the recovered portion of the isocyanate to be prepared is ascertained and compared with the mass (with the hourly mass flow rate in a continuous process regime) of the isocyanate to be prepared which is supplied by the starting material, ascertained as described above. According to the invention, the mass differential ascertained (the differential in the hourly mass flow rate in a continuous process regime) is considered to be attributable to the formation of compounds containing carbodiimide groups, meaning that this mass differential divided by the mass of the distillation residue supplied to the drying apparatus from step c.2) gives the value essential to the invention of the proportion by mass of compounds containing carbodiimide groups based on the total mass of the distillation residue supplied to the drying apparatus.

If the amount of the compounds containing carbodiimide groups formed in situ is large enough to meet the requirements of the invention on the minimum content in the distillation residue, it is possible to dispense with the analytical determination by measurement method I described for case A. Once suitable conditions for step c.2) have been fixed in this way, it is possible in principle to dispense with constant monitoring of the content of compounds containing carbodiimide groups formed in situ during the operation of the drying apparatus used in step c.2). However, it is advisable to conduct control tests to verify the result once ascertained from time to time, in continuous mode especially at least 1× every 720 h, preferably at least 1× every 360 h, more preferably at least 1× every 180 h, most preferably at least 1× every 90 h.

There follows firstly a brief summary of various possible embodiments of the invention:

In a first embodiment of the invention, the phosgenation is conducted in the liquid phase in the presence of a solvent.

In a second embodiment of the invention, the phosgenation is conducted in the gas phase, the phosgenation comprising a quench in which the gaseous process product formed, comprising the isocyanate to be prepared, is cooled by contacting with a quench liquid selected from the group consisting of solvent, the isocyanate to be prepared and mixtures of the isocyanate to be prepared and solvent, and the isocyanate to be prepared is liquefied.

In a third embodiment of the invention, which is a particular configuration of the second embodiment, the quench liquid is selected from the group consisting of solvent and mixtures of the isocyanate to be prepared and solvent.

In a fourth embodiment of the invention, which is a particular configuration of all embodiments in which the use of a solvent is envisaged, this solvent is selected from the group consisting of chlorobenzene, ortho-dichlorobenzene, para-dichlorobenzene, the isomers of trichlorobenzene, toluene, the isomers of xylene and mixtures of the aforementioned solvents.

In a fifth embodiment of the invention, which is likewise a particular configuration of all embodiments in which the use of a solvent is envisaged, any low boilers present consist of solvent and secondary components, where the proportion by mass of secondary components, based on the total mass of the distillation bottom stream, is not more than 0.10% by mass.

A sixth embodiment of the invention, which can be combined with all other embodiments, encompasses step 1), wherein the pre-concentration is effected at a temperature in the range from 120° C. to 180° C. and a pressure in the range from 20 $mbar_{(abs.)}$ to 60 $mbar_{(abs.)}$.

In a seventh embodiment of the invention, which can be combined with all other embodiments, the drying apparatus used in step 2) is an apparatus selected from the group consisting of heated, product-agitating vacuum driers with a horizontal shaft, rotary tubes, disk driers, belt driers and pelletizing screws.

In an eighth embodiment of the invention, which can be combined with all other embodiments, the process of the invention comprises the following steps:
a) phosgenating the primary amine corresponding to the isocyanate to be prepared to obtain a liquid crude process product comprising the isocyanate to be prepared and a hydrogen chloride-comprising gaseous crude process product, with optional use of a solvent;
b) working up the liquid crude process product obtained in step a), comprising the steps of:
b.1) optionally separating dissolved phosgene and dissolved hydrogen chloride from the liquid crude process product obtained in step a) to obtain a phosgene- and hydrogen chloride-depleted liquid process product;
b.2) optionally separating solvent from the liquid crude process product obtained in step a) or from the phosgene- and hydrogen chloride-depleted liquid process product obtained in step b) to obtain a phosgene-, hydrogen chloride- and solvent-depleted liquid process product;
b.3) distilling the liquid crude process product obtained in step a) or the phosgene- and hydrogen chloride-depleted liquid process product obtained in step b.1) or the phosgene-, hydrogen chloride- and solvent-depleted liquid process product obtained in step b.2) to obtain a distillate stream comprising a first portion of the isocyanate to be prepared and a distillate bottom stream consisting of distillation residue, a second portion of the isocyanate to be prepared and optionally low boilers, especially solvent;
wherein the distillation bottom stream obtained in step b.3) is the distillation bottom stream to be worked up in step 2) or in step 1) and step 2).

In a ninth embodiment of the invention, which is especially used from particular configuration of the eighth embodiment, the adjustment of the proportion by mass of compounds containing carbodiimide groups based on the total mass of the distillation residue supplied to the drying apparatus is brought about via exclusively one, two or all of the following measures:
A. establishing process conditions that promote the formation of compounds containing carbodiimide groups in step a) and/or in step b) and/or—if conducted—in step 1);
B. preparing compounds containing carbodiimide groups from the isocyanate to be prepared in a separate operation and supplying the compounds containing carbodiimide groups thus prepared to the drying apparatus from step 2);
C. forming compounds containing carbodiimide groups in situ in step 2).

A tenth embodiment of the invention, which is a particular configuration of the ninth embodiment, includes measure A, wherein the adjustment of process conditions that favor the formation of compounds containing carbodiimide groups in step a) and/or in step b) and/or—if conducted—in step 1) is brought about by an increase in the temperature in the respective step and/or by an increase in the residence time of the process product that passes through the respective step.

An eleventh embodiment of the invention, which is likewise a particular configuration of the ninth embodiment, but can also be employed together with the tenth embodiment and/or the fourteenth embodiment outlined further down, includes measure B, wherein the preparation of compounds containing carbodiimide groups from the isocyanate to be prepared in a separate operation comprises the following:
heating a process product containing the isocyanate to be prepared from the preparation process of the invention
in the absence of catalysts at a temperature in the range from 200° C. to 270° C.
or
in the presence of catalysts of the phospholene oxide at a temperature in the range from 50° C. to 150° C.

In a twelfth embodiment of the invention, which is a particular configuration of the tenth and/or eleventh embodiment, especially when measure C) is dispensed with, step 2) is conducted at a pressure in the range from 10 $mbar_{(abs.)}$ to 250 mbar$_{(abs.)}$, preferably in the range from 20 mbar$_{(abs.)}$ to 200 mbar$_{(abs.)}$, more preferably in the range from 30 mbar$_{(abs.)}$ to 100 mbar$_{(abs.)}$.

A thirteenth embodiment of the invention, which is likewise a particular configuration of the ninth embodiment, but can also be employed together with the tenth embodiment and/or the eleventh embodiment, includes measure C, wherein the drying in step 2) is conducted
  first in a first partial step 2.1) at a pressure in the range from >750 mbar$_{(abs.)}$ to 1013 mbar$_{(abs.)}$ and at a temperature in the range from 200° C. to 270° C. and then in a second partial step 2.2) at a pressure in the range from 10 mbar$_{(abs.)}$ 250 mbar$_{(abs.)}$, preferably 20 mbar$_{(abs.)}$ to 200 mbar$_{(abs.)}$, more preferably 30 mbar$_{(abs.)}$ to 100 mbar$_{(abs.)}$, and at a temperature in the range of 200° C. to 270° C.,
  or
  at a pressure in the range from >250 mbar$_{(abs.)}$ to 750 mbar$_{(abs.)}$, preferably 300 mbar$_{(abs.)}$ to 650 mbar$_{(abs.)}$, more preferably 450 mbar$_{(abs.)}$ to 550 mbar$_{(abs.)}$, and a temperature in the range from 200° C. to 270° C.

In a fourteenth embodiment of the invention, which can be combined with all other embodiments, the isocyanate to be prepared is selected from the group consisting of tolylene diisocyanate, naphthyl diisocyanate, pentane 1,5-diisocyanate, hexamethylene 1,6-diisocyanate, isophorone diisocyanate, xylylene diisocyanate and diisocyanatodicyclohexylmethane.

The embodiments briefly outlined above and further possible configurations of the invention are elucidated in detail hereinafter. For the sake of simplicity, reference is made to the overall process comprising steps a) to c) ("eighth embodiment of the invention"), which does not mean that all possible configurations of the invention outlined hereinafter are restricted to this eighth embodiment. Various embodiments are combinable with one another as desired unless the opposite is apparent to the person skilled in the art from the context.

In step a), the isocyanate to be prepared is first obtained by phosgenating the corresponding primary amine in crude form (i.e. as "the liquid crude process product comprising the isocyanate to be prepared"). The isocyanate to be prepared is preferably a diisocyanate, more preferably a diisocyanate selected from the group consisting of tolylene diisocyanate (TDI hereinafter), naphthyl diisocyanate (NDI hereinafter), pentane 1,5-diisocyanate (PDI hereinafter), hexamethylene 1,6-diisocyanate (HDI hereinafter), isophorone diisocyanate (IPDI hereinafter), xylylene diisocyanate (XDI hereinafter) and diisocyanatodicyclohexylmethane (H12-MDI hereinafter). The primary amines corresponding to the aforementioned isocyanates are tolylenediamine (TDA hereinafter), naphthylenediamine (NDA hereinafter), pentane-1,5-diamine (PDA hereinafter), hexamethylene-1,6-diamine (HDA hereinafter), isophoronediamine (IPDA hereinafter), xylylenediamine (XDA hereinafter) and diaminodicyclohexylmethane (H12-MDA hereinafter). If the amines mentioned may be present in different isomeric forms without explicit specification thereof, all isomer distributions are encompassed in accordance with the invention. If the corresponding primary amine is present as a mixture of various isomers, the isomer distribution of the isocyanate to be prepared, corresponds essentially or entirely to that of the starting amine. In principle, it is also possible to convert mixtures of the aforementioned amines, although this is generally not preferred.

More preferably, the process of the invention is used for preparation of TDI by phosgenation of TDA. The exact isomer composition of the TDA used present in each case is unimportant for the process of the invention. Typically, TDA which is used with preference comprises 78.0% by mass to 82.0% by mass of 2,4-TDA and 18.0% by mass to 22.0% by mass of 2,6-TDA, based on the total mass of the 2,4- and 2,6-TDA isomers. Based on the total mass of the TDA, the 2,4- and 2,6-TDA isomers preferably account for a sum total of 95.0% by mass to 100% by mass, more preferably of 98.0% by mass to 100% by mass.

The phosgenation of a primary amine to give the corresponding isocyanate is known in principle and can be conducted by any of the methods known in the prior art. Examples include the processes described in the following literature references: Ullmann's Encyclopedia of Industrial Chemistry, 5th ed. Vol. A 19, S. 390 ff., VCH Verlagsgesellschaft mbH, Weinheim, 1991, G. Oertel (Ed.) Polyurethane Handbook, 2nd Edition, Hanser Verlag, Munich, 1993, p. 60 ff., G. Wegener et. al. Applied Catalysis A: General 221 (2001), p. 303 to 335, Elsevier Science B.V., EP 1 369 412 A1, EP 1 754 698 B1 and EP 0 289 840 B1.

The reaction of primary amine and phosgene in step a) preferably takes place as follows:

Phosgene is used in a stoichiometric excess, based on the primary amine. The phosgenation can be conducted in the liquid phase and in the gas phase, especially in the gas phase.

Examples of liquid phase phosgenations are described in DE 37 44 001 C1, EP 0 314 985 A1, EP 1369 412 A1, DE-A-102 60 027, DE-A-102 60 093, DE-A 103 10 888, DE-A-10 2006 022 448, US-A 2007/0299279 and the literature cited in each of these.

In a preferred embodiment of step a) as liquid phase phosgenation, the procedure is as follows:

The primary amine and phosgene coreactants are dissolved separately in a solvent. Preferred solvents for this purpose are chlorobenzene, ortho-dichlorobenzene, para-dichlorobenzene, the isomers of trichlorobenzene, toluene and/or the isomers of xylene. Particularly preferred solvents are chlorobenzene and dichlorobenzene; ortho-dichlorobenzene is very exceptionally preferred, especially in conjunction with TDI as the isocyanate to be prepared. The primary amine is preferably used in a concentration of 10% by mass to 40% by mass, preferably of 10% by mass to 20% by mass, based on the total mass of the solution. Phosgene is preferably used in a concentration of 10% by mass to 40% by mass, preferably of 25% by mass to 35% by mass, based on the total mass of the solution.

Efficient mixing of primary amine and phosgene is of high significance in the liquid phase process. For this purpose, static mixing devices (preferably nozzles) and dynamic mixing devices (containing mechanically moving parts) are used in the prior art. After the mixing, the mixed coreactants pass through a reaction zone to complete the conversion. Mixing device and reaction zone may also be disposed in a common reactor. Phosgene is preferably used in a stoichiometric excess over the primary amino groups of the amine, especially in a molar ratio of phosgene to primary amino groups in the range from 4:1 to 1:1, more preferably in the range from 3:1 to 1:1, most preferably in the range from 2:1 to 1:1.

The liquid phase phosgenation can be conducted at various temperature and pressure levels. For example, it is possible to conduct the liquid phase phosgenation at a temperature in the range from 0° C. to 240° C., preferably from 20° C. to 240° C., and at a pressure in the range from 1.0 bar$_{(abs.)}$ to 70 bar$_{(abs.)}$, preferably from 1.0 bar$_{(abs.)}$ to 50 bar$_{(abs.)}$.

The hydrogen chloride formed as a coproduct in the reaction is partly dissolved in the liquid phase and partly outgases. The size of the proportion of the dissolved hydrogen chloride compared to that in gaseous form depends on the chosen temperature and pressure level. In each case, in step a), a liquid stream comprising the isocyanate to be prepared and solvent and a gaseous stream comprising hydrogen chloride and any evaporated solvent are obtained. If phosgene is used in a superstoichiometric amount, both streams additionally contain phosgene. Both streams can be taken directly from the reaction zone. It is also possible to take a biphasic process product (comprising a liquid phase and a gas phase) from the reaction zone and transfer it to an apparatus for phase separation. This phase separation can be effected all apparatuses known to those skilled in the art that are suitable for separation of gas and liquid phases. Preference is given to using gas and liquid separators, for example cyclone separators, deflection separators and/or gravitational separators with or without static separation aid. It is likewise possible to assist the phase separation by reducing the pressure compared to the pressure that exists in the reaction zone owing to enhanced outgassing of hydrogen chloride (and of any other gaseous constituents). The liquid stream taken from the reaction zone or—if present—the liquid stream taken from the apparatus connected downstream of the reaction zone for phase separation, in this embodiment, is the starting material for the workup to be conducted in step b), meaning that this liquid phase, in the terminology of the present invention, is "the liquid crude process product comprising isocyanate to be prepared".

Using the example of the primary amine TDA, the liquid phase phosgenation is outlined in detail hereinafter:

In the liquid phase process, the TDA, optionally already dissolved in an inert solvent defined further up, is supplied to the mixing with phosgene at a temperature in the range from −10° C. to 220° C., preferably from 0° C. to 200° C., more preferably from 20° C. to 180° C. The phosgene can be supplied to the mixing with TDA either without solvent or likewise dissolved in one of the solvents defined further up at a temperature in the range from −40° C. to 200° C., preferably from −30° C. to 170° C., more preferably from −20° C. to 150° C. The mixing of TDA and phosgene, optionally already dissolved in one of the inert solvents defined further up, in the liquid phase method is effected preferably by means of a static mixer or a dynamic mixer. Examples of suitable static mixers include nozzles or nozzle arrangements as described, for example, in DE 17 92 660 A, U.S. Pat. Nos. 4,289,732 or 4,419,295. Examples of suitable dynamic mixers include pump-like aggregates, for example centrifugal pumps (cf. U.S. Pat. No. 3,713,833) or specific mixer reactors (cf. EP 0 291 819 A, EP 0 291 820 A, EP 0 830 894 A).

The reaction in the downstream reaction zone, in the liquid phase method, is effected at a temperature in the range from 0° C. to 250° C., preferably from 20° C. to 200° C., more preferably from 20° C. to 180° C., with an average residence time of the reaction mixture in the reaction zone in the range from 10 s to 5 h, preferably from 30 s to 4 h, more preferably from 60 s to 3 h, and at a pressure of up to 100 $bar_{(abs.)}$, preferably in the range from 1.0 $bar_{(abs.)}$ to 70 $bar_{(abs.)}$, more preferably from 1.0 $bar_{(abs.)}$ to 50 $bar_{(abs.)}$. Examples of process regimes usable in accordance with the invention, with regard to the reaction in the reaction zone, are described, for example, in US-A 2007/0299279 (especially p. 7, paragraphs [0070], [0071], [0089]) and DE-A 103 10 888 (especially p. 5 paragraphs [0038], [0039]) and the documents cited in each.

Examples of gas phase phosgenations are described in EP 0 570 799 A1, EP 1 555 258 A1, EP 1 526 129 A1 and DE 101 61 384 A1, and more particularly for aliphatic isocyanates in EP 0 289 840 B1, EP 1 754 698 B1, EP 1 319 655 B1 and EP 1 362 847 B1. Advantages of this process over the otherwise customary liquid phase phosgenation lie in the energy-saving caused by the minimization of a demanding solvent and phosgene circuit.

In a preferred embodiment of step a) as gas phase phosgenation, the procedure is as follows:

In a step a.1), a gaseous stream of a primary amine is provided. Suitable methods for this purpose are known in principle to those skilled in the art. Preferred embodiments are outlined hereinafter.

The primary amine can be converted to the gas phase in all evaporation apparatuses known from the prior art, especially in a falling-film evaporator. Preference is given to using those evaporation apparatuses in which a small volume of working contents is guided over a falling-film evaporator with a high circulation power.

For minimization of thermal stress on the amine, irrespective of the exact configuration of the evaporation apparatus, it is preferable to assist the evaporation operation by feeding in an inert gas such as $N_2$, He, Ar (especially $N_2$) or the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents.

In addition, the evaporation—and if required superheating—of the starting amine (especially to a temperature in the range from 200° C. to 430° C., preferably 250° C. to 420° C., more preferably 250° C. to 400° C.) is preferably effected in multiple stages in order to avoid unevaporated droplets in the gaseous amine stream. Especially preferred are multistage evaporation and superheating steps in which droplet separators are installed between the evaporation and superheating systems and/or the evaporation apparatuses also have the function of a droplet separator. Suitable droplet separators are known to those skilled in the art.

In a step a.2), a gaseous phosgene stream is provided. Preferably, a molar ratio of phosgene to primary amine groups of 1.1:1 to 20:1, more preferably 1.2:1 to 5.0:1, is established. As described above for the primary amine, the phosgene is preferably also heated to a temperature in the range from 200° C. to 430° C., preferably 250° C. to 420° C., more preferably 250° C. to 400° C., and optionally diluted with an inert gas such as $N_2$, He, Ar (especially $N_2$) or with the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents.

In a step a.3), the primary amine and phosgene coreactants are mixed in a mixing zone and converted in a downstream reaction zone. The separately heated amine and phosgene coreactants are preferably supplied via a nozzle arrangement to the mixing and conversion. The nozzle arrangement for introduction of the amine and phosgene reactant gas streams may be configured in various ways known to the person skilled in the art; examples can be found, for example, in EP 2 199 277 B1, paragraphs [0017] to [0019], EP 1 449 826 B1, paragraphs [0011] to [0012], EP 1 362 847 B1, paragraphs [0011] to [0012], EP 1 526 129 B1, paragraphs [0009] to [0011] and EP 1 555 258 B1, paragraphs [0008] to [0011].

As well as the option already mentioned of diluting the gaseous stream of the primary amine and the gaseous phosgene stream, it is also possible to run a separate diluent gas stream (an inert gas such as $N_2$, He, Ar (especially $N_2$) or the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents) directly into the mixing in step a.3). In this case, this diluent gas stream is preferably heated to a temperature in the range from 100° C. to 500° C., preferably 150° C. to 450° C., more preferably 150° C. to 400° C.

The further conversion in the reaction zone of the primary amine and phosgene coreactants that have been mixed in the mixing zone is preferably effected in an adiabatic manner. Adiabatic conversion means that controlled removal of the heat of reaction formed by a heat carrier medium is dispensed with. Therefore, the reaction enthalpy—apart from unavoidable heat losses—is reflected quantitatively in the temperature differential of product gas stream and reactant gas stream. More particularly, the invention also relates to a process in which step a.3) is conducted adiabatically and wherein composition and temperature of the gaseous stream of the primary amine in step a.1) and the phosgene stream in step a.2) are each chosen such that, in step a.3), a temperature in the range from 250° C. to 450° C., preferably in the range from 270° C. to 425° C., more preferably in the range from 280° C. to 420° C., is established in the mixing zone and in the reaction zone. This means that the temperature at any point in the mixing zone and the reaction zone is within this range.

Mixing zone and reaction zone are disposed here preferably in a common technical apparatus for performance of chemical reactions, the reactor. In this arrangement, mixing zone and reaction zone generally have a fluid transition without the possibility of—as in the case of use of a separate mixing apparatus, which is also possible in principle—strict delimitation between the two. The reaction zone after mixing of the reactants serves to provide delay time in order to assure maximum conversion. Details of the construction of suitable phosgenation reactors are known to those skilled in the art.

In the reaction zone, amine and phosgene are converted rapidly to the corresponding isocyanate, preferably adiabatically as described. The reaction is preferably conducted such that the amine is converted fully before entry into the quench zone described in detail further down.

In a step a.4), rapid cooling and liquefaction (apart from trace contents that remain in the gas phase) of the gaseous process product formed, comprising the isocyanate be prepared ("quench"), is effected by contacting with a quench liquid in a quench zone. Suitable quench liquids are (organic) solvents, the isocyanate to be prepared and mixtures of the isocyanate to be prepared and an (organic) solvent, especially solvent and mixtures of the isocyanate to be prepared and an (organic) solvent. Solvents for the quench are preferably selected from the group consisting of chlorobenzene, ortho-dichlorobenzene, para-dichlorobenzene, the isomers of trichlorobenzene, toluene, the isomers of xylene and mixtures of the aforementioned solvents. Particularly preferred solvents are chlorobenzene and dichlorobenzene; ortho-dichlorobenzene is very exceptionally preferred, especially in conjunction with TDI as the isocyanate to be prepared. The contacting is preferably effected by injecting the quench liquid into the gaseous stream of the reaction product mixture.

Options for the construction and operation of a quench zone are known in principle from the prior art. The apparatuses and methods of the prior art can also be used in the context of the present invention. Possible configurations of the quench zone are disclosed, for example, in EP 1 403 248 A1 and EP 1 935 875 A1.

The temperature of the quench liquid used in step a.4) is preferably chosen such that it is firstly high enough to cleave the carbamoyl chloride corresponding to the isocyanate to isocyanate and hydrogen chloride. (It is in no way certain whether the carbamoyl chloride intermediate known from the liquid phase phosgenation will also be formed in the gas phase phosgenation. Since, however, it is independently conceivable that liquefied isocyanate reacts partly with the hydrogen chloride gas present in the quench to give the carbamoyl chloride, the temperature of the quench liquid should be high enough to suppress this reaction.) On the other hand, isocyanate and any solvent additionally used as diluent in the gaseous amine stream and/or gaseous phosgene stream should very substantially condense or very substantially dissolve in the solvent, while excess phosgene, hydrogen chloride and any inert gas used additionally as diluent pass through the quench zone very substantially uncondensed and undissolved, such that the temperature of the quench liquid chosen must not become too high either. Quench liquids of particularly good suitability for selectively obtaining the isocyanate from the gaseous reaction mixture are those kept at a temperature of 50° C. to 200° C., preferably 80° C. to 180° C.

At a given temperature, pressure and composition, it is easy for the person skilled in the art on the basis of the physical data what proportion by mass of the isocyanate will condense in the quench and what proportion will run through it uncondensed. It is likewise easy to predict what proportion by mass of the excess phosgene, hydrogen chloride, any solvent and any inert gas used as diluent will run through the quench uncondensed and what proportion will dissolve in the quench liquid.

The mixture of reaction product mixture and quench liquid thus obtained in the gas phase therefore contains gaseous components and liquid components, i.e. is biphasic.

In a step a.5), the biphasic mixture of reaction product mixture and quench liquid obtained in step a.4) is guided into a collecting zone for phase separation.

In a preferred embodiment, mixing zone, reaction zone, quench zone and collecting zone are arranged in said sequence from the top downward in an upright, especially conical or cylindrical or conical-cylindrical, reactor. In this embodiment, the mixture of reaction product mixture and quench liquid obtained in step a.4) flows under gravity (i.e. "automatically") into the collecting zone. In another arrangement of the collecting zone, it may be necessary under some circumstances to pump the mixture of reaction product mixture and quench liquid into the collecting zone.

In the collecting zone, a separation of the mixture of reaction product mixture and quench liquid obtained in step a.4) into liquid crude process product and a gaseous crude process product takes place. The liquid crude process product comprises at least the isocyanate to be prepared (and any solvent used as quench liquid, any by-products or unreacted impurities introduced by the coreactants, any dissolved phosgene used in a superstoichiometric amount and any dissolved hydrogen chloride). The gaseous crude process product comprises at least the hydrogen chloride coproduct (and any phosgene used in a superstoichiometric amount, any evaporated solvent, any inert gases and any non-liquefied isocyanate to be prepared). The liquid phase and gaseous phase are preferably withdrawn continuously from the collecting zone. In this embodiment, the liquid phase thus obtaining is the starting material from the workup to be conducted in step b), meaning that this liquid phase is the liquid crude process product comprising isocyanate to be prepared.

After the phosgenation in step a), in step b), the liquid crude process product obtained, comprising the isocyanate to be prepared, is worked up. The crude isocyanate can be worked up by commonly known methods. Examples are described in EP-A-1 413 571, US 2003/0230476 A1 (TDI), and EP 0289 840 B1 (HDI, IDPI and H12-MDI).

Optionally, dissolved phosgene and dissolved hydrogen chloride are first separated from the liquid crude process product obtained in step a) in a separate step b.1). This process regime is preferred especially when the phosgenation in step a) is conducted in the liquid phase because the liquid crude process product obtained in a liquid phase phosgenation tends to contain significantly higher proportions of dissolved phosgene and dissolved hydrogen chloride than that obtained in a gas phase phosgenation. Step b.1) can in principle be conducted in any manner known to those skilled in the art, especially by distillation, absorption or a combination of the two. Possible embodiments are shown further down with reference to different variants.

After step b.1) or—especially in the case of performance of step a) in the gas phase—immediately after step a), there may be a removal of solvent in a separate step b.2). Step b.2) can be conducted in any manner known to those skilled in the art, especially by distillation. Possible embodiments are shown further down with reference to different variants.

In step b.3) of the process of the invention, the isocyanate to be prepared is isolated by distillation. This can in principle be accomplished in any manner known to the person skilled in the art for this purpose. Possible embodiments are shown further down with reference to different variants.

For the configuration of the workup in step b) in detail, various embodiments are possible. Preferred variants are outlined hereinafter using the example of TDI:

Variant 1

Variant 1, which is suitable particularly when step a) is being conducted in the liquid phase, is described in principle in Chem System's PERP Report for TDI/MDI (Chem Systems, Process Evaluation Research Planning TDI/MDI 98/99 S8, Tarrytown, N.Y., USA: Chem Systems 1999, p. 27 to 32). In this variant, the liquid reaction mixture, on completion of distillative removal of hydrogen chloride and phosgene (corresponding to step b.1) in the terminology of the present invention), still contains a solvent content, based on its total mass, of >50% by mass, preferably 51% by mass to 85% by mass, more preferably 55% by mass to 65% by mass. This mixture is sent to a solvent removal (corresponding to step b.2) in the terminology of the present invention), wherein a solvent-TDI mixture is first distilled off into a solvent distillation column in a preliminary evaporator. In the solvent distillation column, solvent is distilled off and sent back to the process. The bottom stream from this solvent distillation contains, based on the total mass of the bottoms, as well as TDI, especially also preferably 15% by mass to 25% by mass of solvent, based on the total mass of this bottom stream. This stream is guided into what is called an intermediate column in which further solvent is distilled off and the bottom product that has been freed of solvent is sent to a last distillation column for purification of the TDI. The latter is operated under reduced pressure and gives the purified saleable isocyanate TDI as distillate stream (corresponding to step b.3) in the terminology of the present invention). A portion of the TDI remains in the distillation bottom stream from this last distillation column. The functions of the intermediate column and the distillation column for TDI purification may also, as described in US 2003/0230476 A1, be combined in a dividing wall column, wherein a vapor stream of low boilers and solvent, a fraction of pure TDI as distillate stream withdrawn in the region of the dividing wall, and a product stream comprising TDI and higher-boiling components (distillation residue) as distillation bottom stream are obtained. The distillation bottom stream from the distillation column for TDI purification or from the dividing wall column that combines the intermediate column and the TDI purification column is worked up to recover TDI. For this purpose, it is possible to guide this stream, as shown in figure II.A.5 of said PERP System Report, into the preliminary evaporator of this solvent distillation. The bottom product from this preliminary evaporator is then guided to the workup to recover TDI present therein. The treatment in the "TDI Residue Processing Facility" shown in Figure II.A.6 in Chem System's PERP Report for TDI/MDI (Chem Systems, Process Evaluation Research Planning TDI/MDI 98/99 S8, Tarrytown, N.Y., USA: Chem Systems 1999, p. 27 to 32) can be replaced by step c) of the present invention. Since, in this embodiment, the starting material supplied to step c), as a result of the feeding of the distillation bottom stream from step b.3) into the preliminary evaporator for the solvent removal from step b.2), still contains solvent (namely especially 2.0% by mass to 10% by mass of solvent, based on the total mass of this starting material), it is preferable to conduct step c.1) and to separate off this solvent therein prior to the drying in step c.2). It will be appreciated that it is also possible to dispense with the feeding of the distillation bottom stream from step b.3) into the preliminary evaporator and to instead feed this distillation bottom stream directly to the workup in step c).

Variant 2

By contrast with variant 1, in this embodiment, the liquid reaction mixture, on completion of distillative removal of hydrogen chloride and phosgene, still contains a solvent content, based on the total mass thereof, of only ≤50.0% by mass. This mixture is sent to a preliminary evaporator, from which a solvent-TDI mixture is distilled off in a distillation column. In this variant, the TDI is already freed of the solvent in the latter distillation column, and so the bottom stream from this distillation column can be guided into the TDI purification column; in this variant, there is therefore one column less than in variant 1. The TDI purification column is operated under reduced pressure and gives the purified saleable isocyanate TDI as distillate stream. The functions of the TDI purification column and the distillation column upstream thereof may also, as described in EP 1 413 571 A1, be combined in a dividing wall column, wherein a vapor stream of low boilers and solvent, a fraction of pure TDI as distillate stream withdrawn in the region of the dividing wall, and a product stream comprising TDI and higher-boiling components (distillation residue) as distillation bottom stream are obtained. The distillation bottom stream from the TDI purification column or the distillation bottom stream from the dividing wall column that combines the TDI purification column and the distillation column upstream thereof is worked up for recovery of TDI. In variant 2 as well, this workup can be conducted according to step c) of the present invention. For this purpose, it is possible to guide this stream into the abovementioned preliminary evaporator. The bottom product from this preliminary evaporator is then guided to the workup to recover TDI present therein. Since, in this embodiment, the starting material supplied to step c), as a result of the feeding of the distillation bottom stream into the preliminary evaporator for the solvent removal, still contains solvent (namely especially 2.0% by mass to 10% by mass of solvent, based on the total mass of this starting material), it is preferable to conduct step c.1) and to separate off this solvent therein prior to the drying in step c.2). It will be appreciated that it is also possible to dispense with the feeding of the distillation bottom stream from step b.3) into the preliminary evaporator and to instead feed this distillation bottom stream directly to the workup in step c).

Variant 3

Variant 3 comprises the distillation sequences described in variants 2 and 1, but without the preliminary evaporator mentioned in each case, which is supplied with a liquid bottoms discharge from the workup in step c). In this case, the proportion of distillation residue in the distillation sequences described is included in the liquid mass flows up to the respective last TDI purification column. This process is likewise known in principle (EP 1 717 223 A2). In this case, the complete discharge of the distillation residue is effected via the distillation bottom stream of the last distillation column (which can also be assigned to step b.3) in the terminology of the present invention). In variant 3 as well, the workup of this distillation bottom stream can be conducted according to step c) of the present invention.

Variant 4

This variant is used especially when step a) is conducted in the gas phase. Since the liquid crude process product obtained in a gas phase phosgenation contains dissolved phosgene and dissolved hydrogen chloride in a comparatively minor amount (i.e. compared to the liquid phase phosgenation) at most, it is possible to dispense with a separate removal of hydrogen chloride and phosgene in step b.1). The liquid crude process product is either sent directly to a solvent removal (corresponding to step b.2)) in which solvent and any dissolved hydrogen chloride and any dissolved phosgene are removed by distillation overhead, or—if the solvent content is sufficiently low—it is sent directly to a TDI purification column. In both cases, the TDI purification column is preferably configured as a dividing wall column. Low boilers (i.e. lower-boiling by-products than TDI, any hydrogen chloride still present and any phosgene still present, any solvent and any inert gases) are drawn off as vapors overhead. The purified TDI is removed as distillate stream in the region of the dividing wall. The distillation bottom stream obtained comprises the distillation residue and a certain amount of TDI which, in order to keep the distillation bottom stream processable, is not distilled off, and possibly traces of solvent. Rather than a dividing wall column, it is of course also possible to use two series-connected distillation columns without a dividing wall.

In this variant, the solvent removal in step b.2)—if conducted—is preferably conducted at a temperature in the range from 160° C. to 200° C. and at a pressure in the range from 160 mbar to 220 mbar, both figures relating to the bottoms from the distillation column used. In this way, a bottom stream containing, based on the total mass thereof, preferably 9% by mass to 20% by mass of solvent, 79% by mass to 90% by mass of TDI and 1% to 5% by mass of higher-boiling compounds than TDI is obtained.

The TDI purification in step b.3), especially in the case of performance in a dividing wall column, is preferably conducted at a temperature in the range from 160° C. to 200° C. and at a pressure in the range from 50 mbar to 100 mbar, both figures relating to the bottoms from the distillation column used. In this way, a distillation bottom stream containing, based on the total mass thereof, preferably 0.00% by mass to 1.00% by mass of solvent, 80.0% by mass to 95.0% by mass of TDI and 4.00% to 20.0% by mass of higher-boiling compounds than TDI is obtained.

Irrespective of the exact configuration of step b), in step b.3), in all possible process regimes, (at least) one distillate stream comprising a first portion of the isocyanate to be prepared and (at least) one distillation bottom stream comprising a second portion of the isocyanate to be prepared and distillation residue are obtained. The workup of the distillation bottom stream is the subject of step c) of the present invention and is elucidated in detail further down. As elucidated in variants 1 and 2, it is also possible to feed step c), together with the distillation bottom stream from step b.3), also with further bottom streams.

As well as the liquid crude process product, the workup of which has been outlined above, in step a), a gaseous crude process product is also obtained, which is preferably likewise worked up, especially in order to send the hydrogen chloride coproduct formed to an economically viable utilization. The gaseous crude process product comprises at least the hydrogen chloride coproduct (and any phosgene used in a superstoichiometric amount, any evaporated solvent, any inert gases and any non-liquefied isocyanate to be prepared). This gaseous product stream is preferably sent to a further workup in which hydrogen chloride is purified. Any phosgene and solvent constituents still present in the gas stream are separated from one another. The hydrogen chloride recovered can be sent to various possible uses, for example an oxychlorination of ethylene to ethylene dichloride or a recycling process that affords chlorine, which can be recycled back into the isocyanate process. These recycling processes include the catalytic oxidation of hydrogen chloride, for example by the deacon process, the electrolysis of gaseous hydrogen chloride and the electrolysis of an aqueous solution of hydrogen chloride (hydrochloric acid). Any phosgene recovered is preferably reused in step a). Any solvent recovered is preferably likewise reused in step a) (for example as solvent for the primary amine and phosgene coreactants in a liquid phase phosgenation or in the quench of a gas phase phosgenation).

The workup of the distillation bottom stream obtained in step b.3) is the subject of step c) (steps c.1) and c.2) of the process of the invention. This distillation bottom stream consists, in addition to proportions of the isocyanate to be prepared (which are to be recovered as far as possible) and any proportions of solvent, of the distillation residue.

It is preferable to pre-concentrate the distillation bottom stream at first in a step c.1), i.e. to already partly separate off the isocyanate to be prepared by evaporation without solidification of the remaining liquid stream. This pre-concentration by partial evaporation can in principle be effected in any evaporators known to those skilled in the art. More preferably, step c.1) is conducted in an evaporator selected from the group consisting of thin-film evaporators, climbing-film evaporators, falling-film evaporators, long tube evaporators, helical tube evaporators, forced circulation flash evaporators and a combination of these apparatuses. Particular preference is given here to falling-film evaporators. It is also possible to connect multiple evaporators in series. The pre-concentration in step c.1) is preferably effected at a temperature in the range from 120° C. to 180° C. and at a pressure in the range from 20 mbar$_{(abs.)}$ to 60 mbar$_{(abs.)}$, more preferably at a temperature in the range from 130° C. to 175° C. and at a pressure in the range from 25 mbar$_{(abs.)}$ to 45 mbar$_{(abs.)}$. Step c.1) can be conducted continuously or batchwise. The continuous process regime is preferred.

In step c.2), according to the invention, the pre-concentrated liquid stream that has been depleted of isocyanate to be prepared and is obtained in step c.1) or—when step c.1) is dispensed with—the distillation bottom stream obtained in step b.3) is dried. This drying is conducted at a temperature in the range from 150° C. to 500° C., preferably in the range from 185° C. to 300° C., more preferably in the range from 200° C. to 270° C., in a drying apparatus. Drying apparatuses suitable for step c.2) are preferably selected from the group consisting of heated, product-agitating vacuum driers with a horizontal shaft (preferably kneader-driers, paddle driers, shovel driers; wherein each of the driers mentioned may have exactly one shaft or multiple shafts, especially two shafts), rotary tubes, disk driers, belt driers and pelletizing screws. In the drying, the isocyanate to be prepared is evaporated and recovered. What remains is a solid that consists virtually exclusively of distillation residue and still contains the isocyanate to be prepared in traces at most (preferably not more than 1.0% by mass of the isocyanate to be prepared, more preferably not more than 0.1% by mass of the isocyanate to be prepared, based in each case on the total mass of the solids obtained in step c.2). The solid is preferably discharged continuously from the drying apparatus.

According to the invention, the proportion by mass of compounds containing carbodiimide groups based on the total mass of the distillation residue introduced into the drying in step c.2) is adjusted to a value of at least 15%, preferably of at least 20%, more preferably of at least 30%. This can be accomplished as follows:

Case A: The process conditions in step a) and/or in step b) and/or—if conducted—step c.1) promote the formation of compounds containing carbodiimide groups and are especially chosen such that the mass of compounds containing carbodiimide groups introduced into this step from step c.2) via the starting material is sufficiently great that the demands of the invention on the minimum proportion by mass of containing carbodiimide groups in the distillation residue are fulfilled.

Case A is preferred especially when the phosgenation in step a) is effected in the liquid phase. The formation of compounds containing carbodiimide groups is promoted by high temperatures. Therefore, an increase in temperature and/or an increase in the dwell time—each by comparison with the operating state with insufficient carbodiimide formation—in step a) and/or in step b) and/or—if conducted—in step c.1) can increase the proportion of compounds containing carbodiimide groups. The extent to which the temperature and/or the dwell time have to be increased can be determined easily by the person skilled in the art by simple preliminary tests.

Case B: Compounds containing carbodiimide groups are prepared in a separate process from the isocyanate to be prepared and sent to step c.2), especially in such an amount that the requirements of the invention are fulfilled. This case is preferred especially when step a) is conducted in the gas phase.

In one embodiment of the invention, compounds containing carbodiimide groups are prepared by heat-treating a process product containing the isocyanate to be prepared from the preparation process of the invention (especially a portion of the distillate stream obtained in step b.3) or—if conducted—a proportion of the liquid process product depleted of phosgene, hydrogen chloride and solvent which is obtained in step b.2)) at elevated temperature, especially at a temperature in the range from 200° C. to 270° C., for a period of especially 30 minutes to 10 hours. Rather than a purely thermal treatment, the carbodiimidization can also be induced catalytically. Suitable catalysts are especially catalysts of the phospholene oxide type. In the context of the present invention, catalysts of the phospholene oxide type are understood to mean 1-oxophosphacyclopentenes substituted on the phosphorus atom, cyclo-C$_4$H$_6$P(O)R, where the substituent R is a saturated or unsaturated, optionally substituted, especially halogen-substituted, organic radical, especially methyl or phenyl. The catalysts of the phospholene oxide type are known, for example, from EP-A-0 515 933 and U.S. Pat. No. 6,120,699. Typical examples of these catalysts are especially the mixtures of the phospholene oxides known from the prior art of the formula:

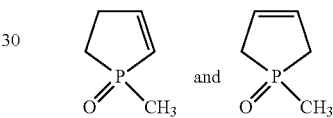

The amount of catalyst necessary in each case can be ascertained by the person skilled in the art in a simple manner in preliminary tests. The carbodiimidization in the presence of a catalyst is preferably conducted at a temperature in the range from 50° C. to 150° C., preferably in the range from 60° C. to 100° C. The proportion of the distillate stream obtained in step b.3) or—if conducted—of the liquid process product depleted of phosgene, hydrogen chloride and solvent which is obtained in step b.2), which, as described, is subjected to a thermally or catalytically induced carbodiimidization, can be determined easily by the person skilled in the art by routine experiments The remaining portion of distillate stream obtained in step b.3) is used further in the customary manner (e.g. sale, conversion to polyurethanes, conversion to prepolymers, blending with other isocyanates to give blends and the like). The remaining portion of any liquid process product depleted of phosgene, hydrogen chloride and solvent and obtained in step b.2) which is used is distilled in step b.3). The process product obtained after the carbodiimidization has ended is mixed with the pre-concentrated liquid stream obtained in step c.1) or—if step c.1) is dispensed with—with the distillation bottom stream obtained in step b.3) prior to supply thereof to the drying apparatus from step c.2), or the process product obtained after carbodiimidization has ended is supplied to this drying apparatus via a separate inlet stub.

In another embodiment, carbodiimidized isocyanate is taken from another preparation process for the same isocyanate to be prepared. It is possible, for example, to mix the distillation bottom stream from step b.3) or the pre-concentrated liquid stream from step c.1) from a production plant in which the production conditions promote the formation of compounds containing carbodiimide groups wholly or partly with the corresponding streams from another production plant in which the production conditions are detrimental to the formation of compounds containing carbodiimide groups, or to feed it directly to step c.2) in this latter production plant.

If the drying in step c.2) is not conducted in accordance with one of the two embodiments outlined in detail hereinafter for case C, it is preferable to maintain a pressure in the drying apparatus from step c.2), for the duration of this step, within the range from 10 mbar$_{(abs.)}$ to 350 mbar$_{(abs.)}$, more preferably in the range from 20 mbar$_{(abs.)}$ to 200 mbar$_{(abs.)}$, most preferably in the range from 30 mbar$_{(abs.)}$ to 100 mbar$_{(abs.)}$. This is accordingly true of every conceivable combination of cases A and B.

Case C: Compounds containing carbodiimide groups are formed in situ in step c.2), especially in a sufficient amount to fulfill the requirements of the invention. This can be accomplished in two ways. Two preferred embodiments are outlined hereinafter:

In a first embodiment, the drying in step c.2) is first conducted in a first partial step c.2.1) at relatively high pressure before, at a later juncture, the pressure is lowered in a second partial step c.2.2). What is enabled in this way is that, prior to the commencement of the "actual" drying operation, compounds containing carbodiimide groups are formed in a sufficient amount in the second partial step at low pressure. In the case of continuous performance of step c.2), partial step c.2.2) is preferably conducted in a dedicated apparatus connected downstream of the apparatus for partial step c.2.1). The first partial step of step c.2) of this embodiment is preferably conducted at a pressure in the range from >750 mbar$_{(abs.)}$ to 1013 mbar$_{(abs.)}$ and at a temperature in the range from 200° C. to 270° C. for a period of especially 30 minutes to 10 hours. Thereafter, the pressure in the second partial step is lowered to a value in the range from 10 mbar$_{(abs.)}$ to 250 mbar$_{(abs.)}$, preferred 20 mbar$_{(abs.)}$ to 200 mbar$_{(abs.)}$, more preferably 30 mbar$_{(abs.)}$ to 100 mbar$_{(abs.)}$. The temperature is preferably in the same range as in the first partial step (i.e. in the range from 200° C. to 270° C.) and is more preferably unchanged compared to the temperature in the first partial step. The second partial step is preferably conducted for a period of 30 minutes to 360 minutes. The transition from the high-pressure phase to the low-pressure phase can also be continuous with gradual lowering of pressure.

In a second embodiment, over the (entire) step c.2), a pressure that permits both sufficient formation of compounds containing carbodiimide groups and the drying of the distillation bottom stream is maintained. In this embodiment, step c.2) is preferably at a pressure in the range from >250 mbar$_{(abs.)}$ to 750 mbar$_{(abs.)}$ preferably 300 mbar$_{(abs.)}$ to 650 mbar$_{(abs.)}$, more preferably 450 mbar$_{(abs.)}$ to 550 mbar$_{(abs.)}$. The wording "over the (entire) step c.2)" does of course also encompass embodiments in which the desired target pressure is established not immediately within the ranges mentioned but, for instance, only after a heating phase. The temperature (for all pressure ranges) is preferably in the range from 200° C. to 270° C. In this embodiment, step c.2) is preferably conducted for a period of 30 minutes to 600 minutes.

In case C), a certain yield loss of isocyanate to be prepared via the in situ carbodiimidization is unavoidable. If, however, operationally stable drying can be achieved as a result, the advantages outweigh this unavoidable disadvantage.

In a preferred embodiment, in step c.2), a separating agent is added in order to facilitate the formation of nontacky dried residue particles. This is true regardless of whether case A, B or C exists. Such separating agents may be additives that are nontacky at the temperature in the reactor, i.e. do not stick together to form larger agglomerates, do not react with the isocyanate and do not hinder the polymerization reaction of the oligomeric constituents of the original distillation residue. Preferably, the separating agent is selected from the group consisting of bitumen, talc, chalk, inorganic pigments and fully dried residue. Among the inorganic pigments, preference is given especially titanium dioxide, iron oxides, aluminum oxide and other metal oxides. Completely dried residue means the solid process product obtained in the drying apparatus from step c.2). This is because it is possible in an appropriate manner to recycle a portion of the solid obtained by drying in step c.2) as separating agent into the drying process. This recycled proportion can also be finely ground.

The drying in step c.2)—irrespective of whether case A, B or C exists—can be conducted batchwise or continuously. In batchwise mode, several drying apparatuses are appropriately operated in parallel in order to avoid interrupted production as a result of the need to remove the solid process product formed after drying has ended. In a continuous process regime, which is appropriate especially on the industrial scale, the solid process product formed is discharged continuously from the drying apparatus by suitable discharge devices (e.g. screw conveyors, paddle conveyors, overflow over a weir or gravitational conveying), especially in the form of a pelletized material or powder. The proportion of the isocyanate to be prepared that has been obtained in this way in step c.2) is preferably combined partly to fully, preferably fully, with the portion of the isocyanate to be prepared that is obtained as distillate stream in step b) and sent to further use. It is likewise possible to feed in the proportion of the isocyanate to be prepared that is obtained in step c.2) at another point in the process, for example in step b), especially to the feed or to the distillation bottom stream of the distillation column used in step b.3) (in the case of multiple distillation columns connected in series preferably into the feed or into the distillation bottom stream of the last distillation column). It is possible to proceed in the same manner with any proportion of isocyanate to be prepared which is obtained in step c.1). Preferably, the proportions of isocyanate to be prepared that are obtained in step c.1) and step c.2) are combined.

EXAMPLES

The examples which follow were conducted in a List drying apparatus (DTB 6500) from 1977. This machine is a single-shaft kneader with a capacity of 6.5 L. The electrical drive has a power of max. 7.5 kW; the shaft speed is variable. The working space of the kneader-drier is equipped with an outer shell and is heated with oil; the return temperature of the oil is measured and indicated. The vapors formed during the drying are condensed in a water-cooled heat exchanger and collected in a scaled receiver. The vacuum is generated by means of a membrane pump and regulated via a vacuum controller. The drying step (c.2)) was conducted batchwise. Percentages are % by mass based on the total mass of the respective process product.

Example 1 (Comparative)

The pre-concentrated liquid stream obtained in a falling-film evaporator connected downstream of the last distillation column for the workup of the liquid crude process product from a phosgenation was dried together with 2.8% by mass of bitumen, based on the mass of the distillation residue present in this pre-concentrated liquid stream, in the drying apparatus at 235° C. (oil return temperature) and 40 mbar$_{(abs.)}$. The pre-concentrated liquid stream to be dried had the following composition:

Distillation residue: 32.6%,
Carbodiimide content in this distillation residue: 2.8%.

The progression of the experiment is shown as a graph in FIG. 1. In the course of drying, there was a significant rise in torque on the shaft of the drying apparatus, recognizable by the maximum in the power curve and the large area beneath this maximum. The energy introduced as a result caused the temperature to rise even above the oil return temperature temporarily. 98.7% of the TDI containing in the pre-concentrated liquid stream to be dried was recovered. This is used to calculate, by measurement method III, the proportion by mass of compounds containing carbodiimide groups in the distillation residue in the context of the present invention to be 5.2%. In this example, there was thus basically in situ carbodiimidization, but to much too small a degree.

Example 2 (Inventive)

The pre-concentrated liquid stream obtained in a falling-film evaporator connected downstream of the last distillation column for the workup of the liquid crude process product from a phosgenation was dried together with 2.8% by mass of bitumen, based on the mass of the distillation residue present in this pre-concentrated liquid stream, in the drying apparatus at 233° C. (oil return temperature) and 40 mbar$_{(abs.)}$. The pre-concentrated liquid stream to be dried had the following composition:

Distillation residue: 30.0%,
Carbodiimide content in this distillation residue: 21.8%.

Figure 2:
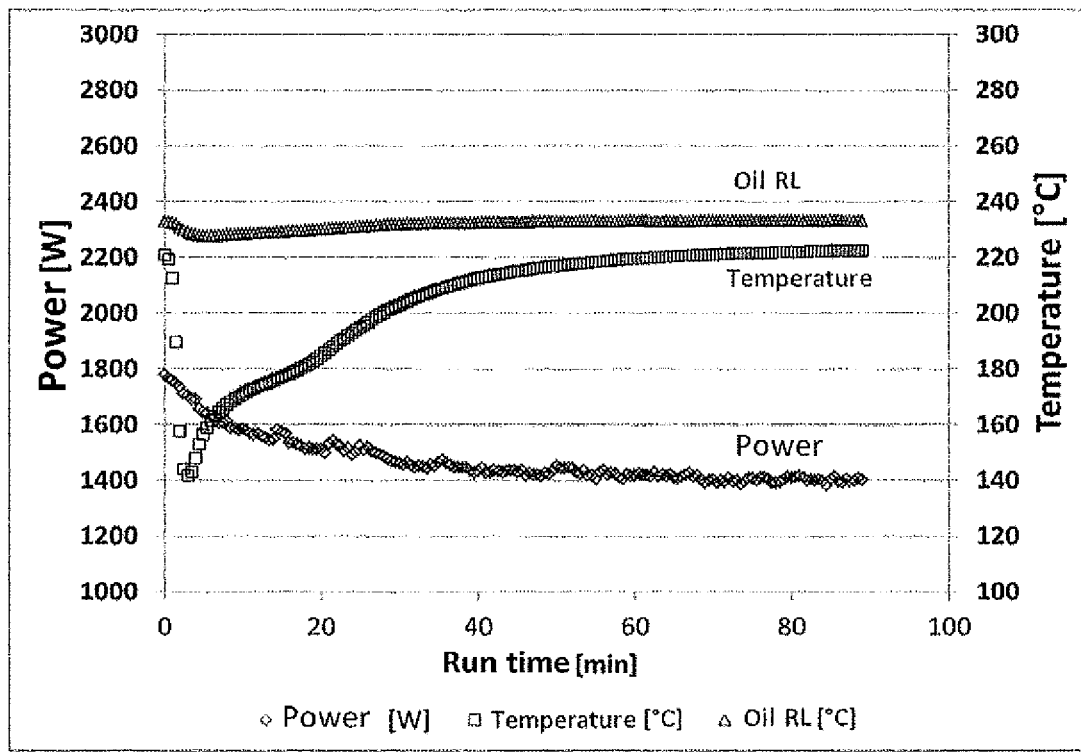
FIG. 2 is a graph illustrating the progression of the experiment of Example 2.

The progression of the experiment is shown as a graph in FIG. 2. In the course of drying, there was no rise in torque on the shaft of the drying apparatus, recognizable by the horizontal progression of the power curve. Moreover, the mechanical energy input was distinctly reduced, and so there was no rise in temperature above the oil return temperature; instead, the temperature approached the oil return temperature in an asymptotic manner. >99% of the TDI containing in the pre-concentrated liquid stream to be dried was recovered.

Example 3 (Inventive)

The experiment was conducted as in example 1, except that the pre-concentrated liquid stream from the falling-film evaporator was introduced into the drying apparatus with the added bitumen and subjected to thermal treatment at 230° C. and 800 mbar$_{(abs.)}$ for 3 hours. Subsequently, the pressure in the drying device was lowered gradually and the pre-concentrated liquid stream was dried in the drying apparatus at 235° C. (oil return temperature) and 40 mbar$_{(abs.)}$.

Figure 3:
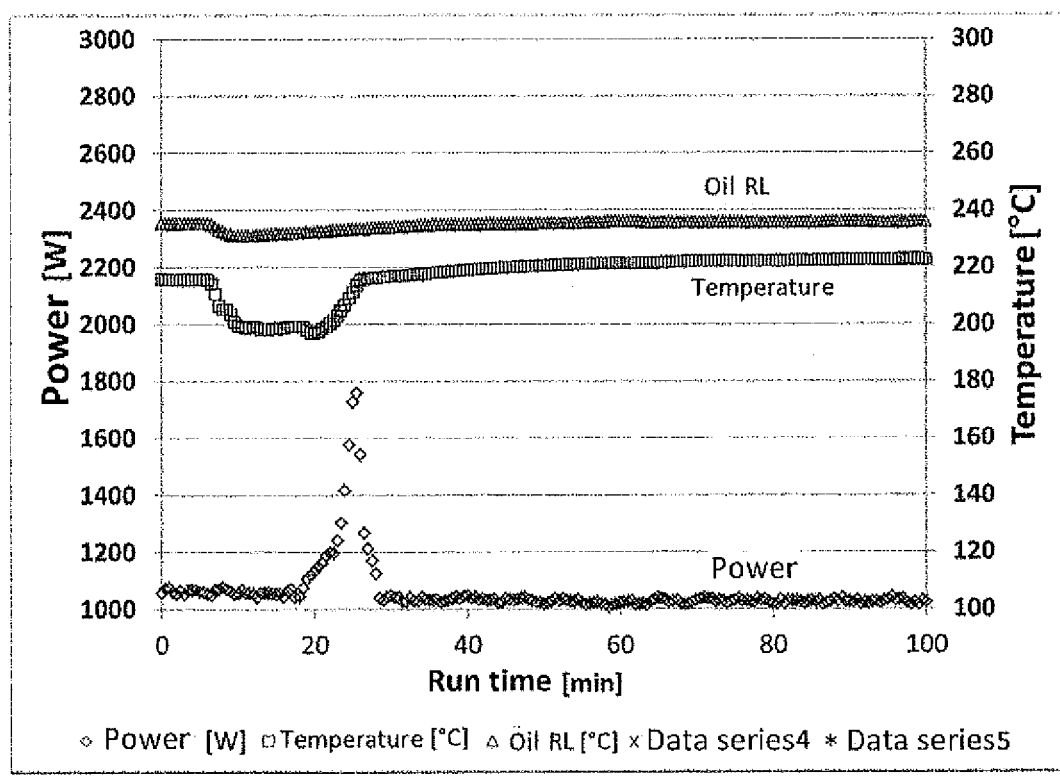
FIG. 3 is a graph illustrating the progression of the experiment of Example 3.

The progression of the experiment is shown as a graph in FIG. 3. In the course of drying, there was a significant rise in torque on the shaft of the drying apparatus, but this rise was very brief. At the same time, a steep temperature rise was observed, but was stopped by the breakup into the solid phase. This distinctly reduced the mechanical energy input, and so there was no further rise in the temperature above the oil return temperature. 87.2% of the TDI containing in the pre-concentrated liquid stream to be dried was recovered. This is used to calculate, by measurement method III, the proportion by mass of compounds containing carbodiimide groups in the distillation residue in the context of the present invention to be 25.9%.

Example 4 (Inventive)

Treatment of TDI at 220° C. for 12 hours produced a TDI-carbodiimide mixture with a carbodiimide content based on the total mass of ~15%. TDI was removed by distillation from this mixture and the carbodiimide content was thus increased to 46.5%. This mixture was then mixed with the pre-concentrated liquid stream from example 1 and dried together with 2.6% by mass of bitumen, based on the mass of the distillation residue present in the pre-concentrated liquid stream, in the drying apparatus at 234° C. (oil return temperature) and 40 mbar$_{(abs.)}$. The blended, pre-concentrated liquid stream to be dried had the following composition:

Distillation residue 34.6%,
Carbodiimide content in this distillation residue 20.0%.

Figure 4:
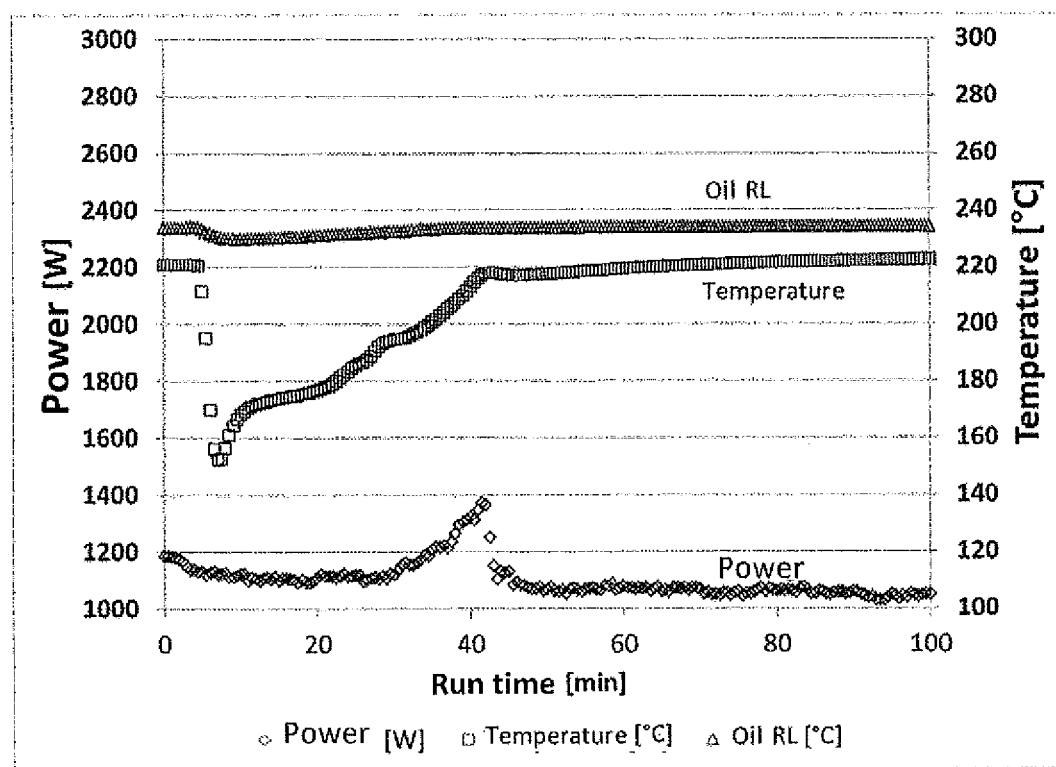
FIG. 4 is a graph illustrating the progression of the experiment of Example 4.

The progression of the experiment is shown as a graph in FIG. 4. In the drying, there was a brief rise in torque on the shaft of the drying apparatus, but this was much less marked than in example 1. The overshooting of the temperature above the oil return temperature was not observed either. >99% of the TDI containing in the pre-concentrated liquid stream to be dried was recovered.

Example 5 (Inventive)

Treatment of TDI at 220° C. for 12 hours produced a TDI-carbodiimide mixture with a carbodiimide content based on the total mass of 15%. TDI was removed by distillation from this mixture and the carbodiimide content was thus increased to 46.5%. This mixture was then mixed with the pre-concentrated liquid stream from example 1 and dried together with 2.6% by mass of bitumen, based on the mass of the distillation residue present in the pre-concentrated liquid stream, in the drying apparatus at 234° C. (oil return temperature) and 40 mbar$_{(abs.)}$. The blended, pre-concentrated liquid stream to be dried had the following composition:

Distillation residue 35.7%,
Carbodiimide content in this distillation residue 30.9%.

Figure 5:
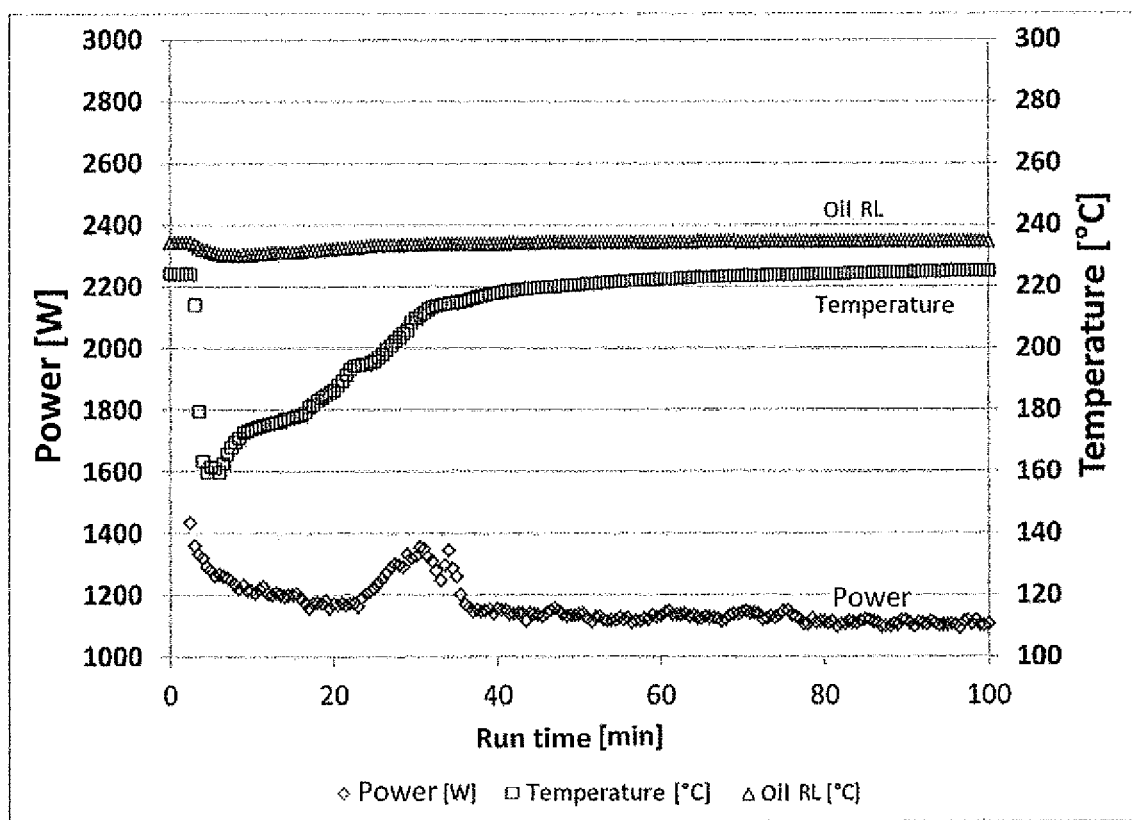
FIG. 5 is a graph illustrating the progression of the experiment of Example 5.

The progression of the experiment is shown as a graph in FIG. 5. In the drying, there was a brief rise in torque on the shaft of the drying apparatus, but this was much less marked as in example 4. The overshooting of the temperature above the oil return temperature was not observed either. >99% of the TDI containing in the pre-concentrated liquid stream to be dried was recovered.

Example 6 (Inventive)

The pre-concentrated liquid stream obtained in a falling-film evaporator connected downstream of the last distillation column for the workup of the liquid crude process product from a phosgenation was dried together with 2.8% by mass of bitumen, based on the mass of the distillation residue present in the pre-concentrated liquid stream, in the drying apparatus at 258° C. (oil return temperature) and 460 mbar$_{(abs.)}$. The pre-concentrated liquid stream to be dried had the following composition:

Distillation residue: 32.6%,

Carbodiimide content in this distillation residue: 2.8%.

The experiment was conducted as in example 1, except that the pre-concentrated liquid stream was dried in the drying apparatus at 258° C. (oil return temperature) and 460 mbar$_{(abs.)}$.

Figure 6:
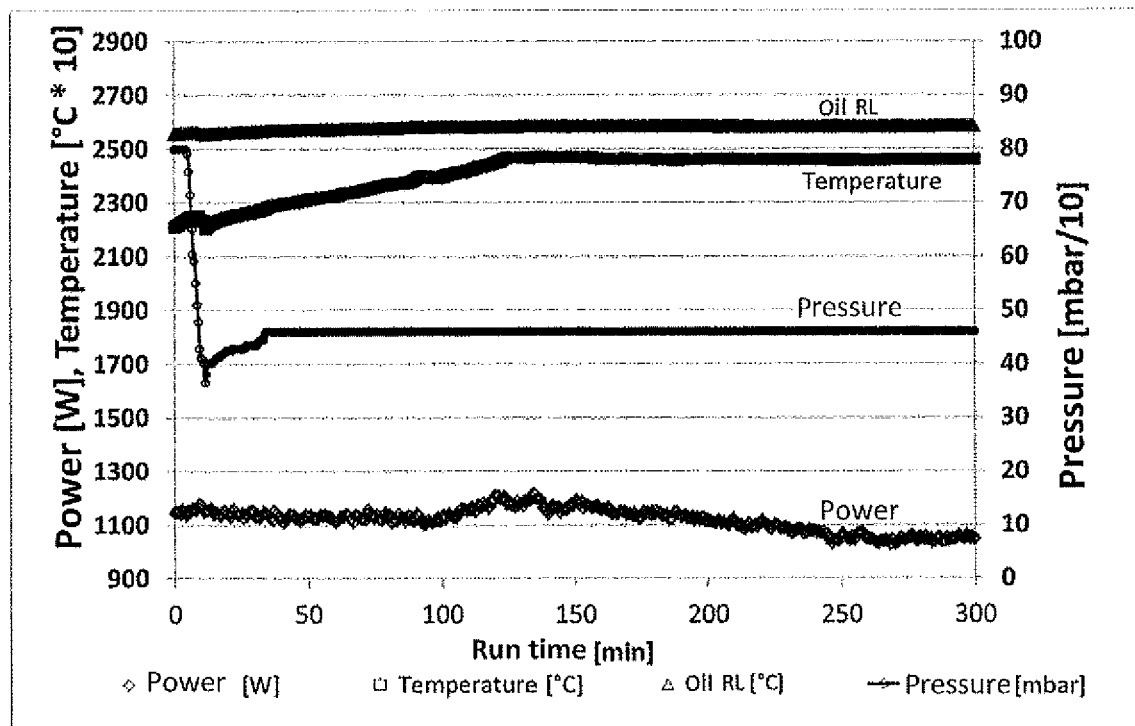
FIG. 6 is a graph illustrating the progression of the experiment of Example 6.

The pre-concentrated liquid stream to be dried was sucked into the preheated drying apparatus. On attainment of 220° C. in the drying apparatus, the vacuum was adjusted to the target value of 460 mbar$_{(abs.)}$. The progression of the experiment is shown as a graph in FIG. 6. In the course of drying, there was a no rise in torque on the shaft of the drying apparatus, recognizable by the horizontal progression of the power curve. Moreover, the mechanical energy input was distinctly reduced, and so there was no rise in temperature above the oil return temperature; instead, the temperature approached the oil return temperature in an asymptotic manner. 64.6% of the TDI containing in the pre-concentrated liquid stream to be dried was recovered. This is used to calculate, by measurement method III, the proportion by mass of compounds containing carbodiimide groups in the distillation residue in the context of the present invention to be 66.7%.

Example 7 (Inventive)

The experiment was conducted as in example 6, except that the pre-concentrated liquid stream was dried in the drying apparatus at 258° C. (oil return temperature) and 300 mbar$_{(abs.)}$. On attainment of a temperature of 230° C. in the drying apparatus, the vacuum was adjusted to the target value of 300 mbar$_{(abs.)}$.

Figure 7:
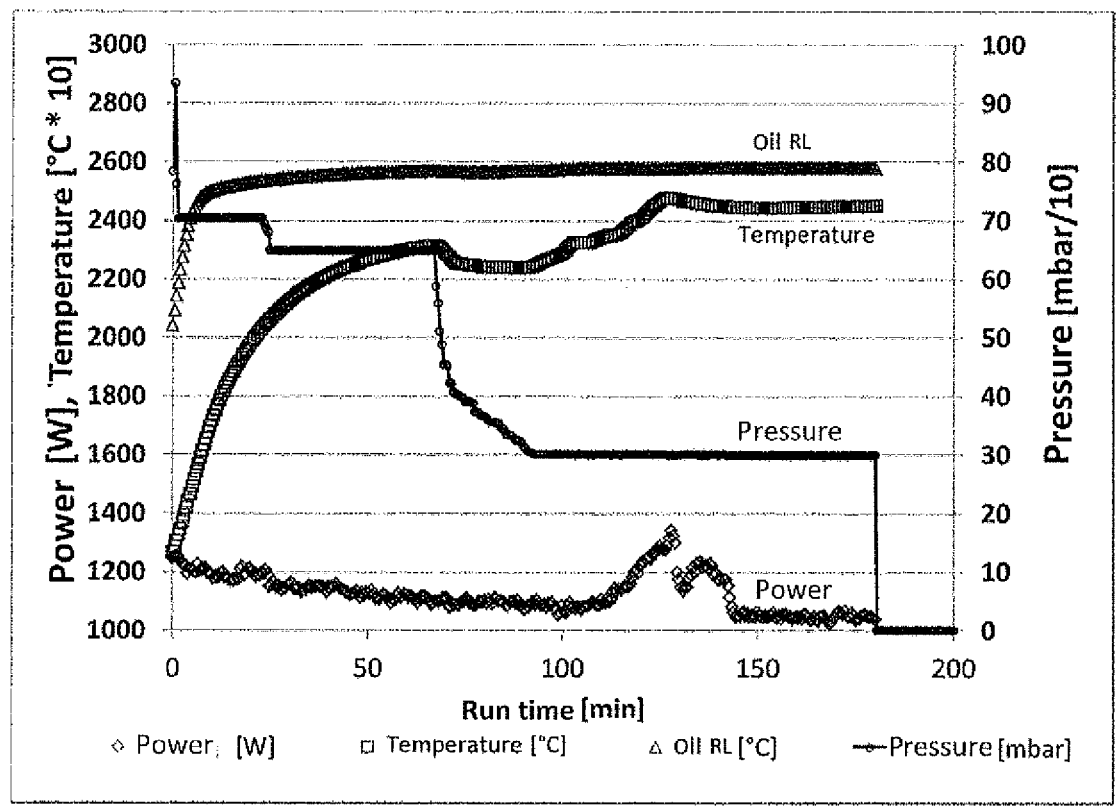
FIG. 7 is a graph illustrating the progression of the experiment of Example 7.

The progression of the experiment is shown as a graph in FIG. 7. In the course of drying, there was a no rise in torque on the shaft of the drying apparatus, recognizable by the horizontal progression of the power curve. Moreover, the mechanical energy input was distinctly reduced, and so there was no rise in temperature above the oil return temperature; instead, the temperature approached the oil return temperature in an asymptotic manner. 82.2% of the TDI containing in the pre-concentrated liquid stream to be dried was recovered. This is used to calculate, by measurement method III, the proportion by mass of compounds containing carbodiimide groups in the distillation residue in the context of the present invention to be 34.9%.

Example 8 (Inventive)

The experiment was conducted as in example 6, except that the was dried in the drying apparatus at 278° C. (oil return temperature) and 300 mbar$_{(abs.)}$. On attainment of a temperature of 250° C. in the drying apparatus, the vacuum was adjusted to the target value of 300 mbar$_{(abs.)}$.

Figure 8:
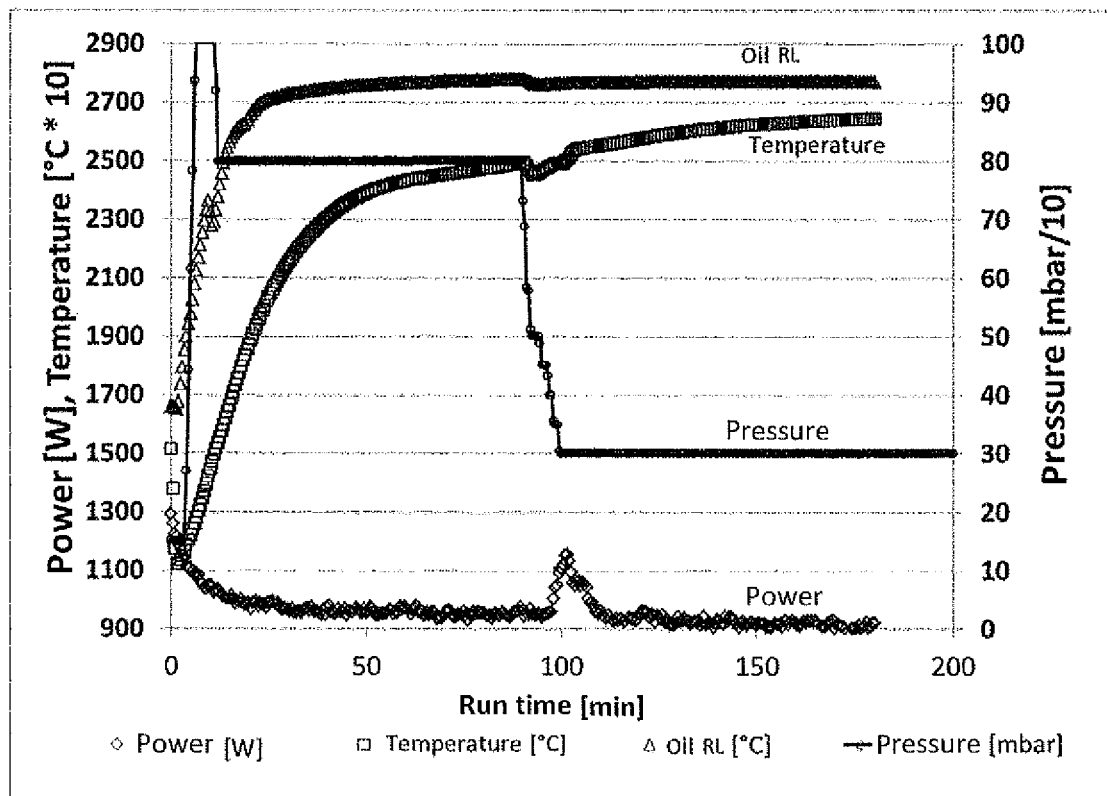
FIG. 8 is a graph illustrating the progression of the experiment of Example 8.

The progression of the experiment is shown as a graph in FIG. 8. In the course of drying, there was a no rise in torque on the shaft of the drying apparatus, recognizable by the horizontal progression of the power curve. Moreover, the mechanical energy input was distinctly reduced, and so there was no rise in temperature above the oil return temperature; instead, the temperature approached the oil return temperature in an asymptotic manner. 80.2% of the TDI containing in the pre-concentrated liquid stream to be dried was recovered. This is used to calculate, by measurement method III, the proportion by mass of compounds containing carbodiimide groups in the distillation residue in the context of the present invention to be 38.5%.

The invention claimed is:

1. A process for preparing an isocyanate by phosgenating the primary amine corresponding to the isocyanate to be prepared to obtain a liquid crude process product comprising isocyanate to be prepared, comprising:
    working up said liquid crude process product to obtain a distillation bottom stream consisting of:
        the isocyanate to be prepared,
        optionally low boilers, and
        distillation residue; and
    working up said distillation bottom stream, said workup comprising:
    1) optionally pre-concentrating the distillation bottom stream in an evaporator by partially evaporating the isocyanate to be prepared which is present in the distillation bottom stream to obtain a pre-concentrated liquid stream depleted of isocyanate to be prepared;
    2) drying the distillation bottom stream or the pre-concentrated liquid stream depleted of isocyanate to be prepared which has been obtained in step 1) in a drying apparatus at a temperature in the range from 150° C. to 500° C. with evaporation and recovery of isocyanate to be prepared to form a solid process product, where the proportion by mass of compounds containing carbodiimide groups based on the total mass of the distillation residue supplied to the drying apparatus is adjusted to a value of at least 15%.

2. The process of claim 1, in which the phosgenation is conducted in the liquid phase in the presence of a solvent.

3. The process of claim 1, in which the phosgenation is conducted in the gas phase, the phosgenation comprising a quench in which the gaseous process product formed, comprising isocyanate to be prepared, is cooled and the isocyanate to be prepared liquefied by contacting with a quench liquid selected from the group consisting of a solvent, the isocyanate to be prepared, and a mixture of the isocyanate to be prepared and a solvent.

4. The process of claim 1, in which the phosgenation is conducted in the gas phase, the phosgenation comprising a quench in which the gaseous process product formed, comprising isocyanate to be prepared, is cooled and the isocyanate to be prepared liquefied by contacting with a quench liquid is selected from the group consisting of a solvent and a mixture of the isocyanate to be prepared and a solvent.

5. The process of claim 2, in which the solvent is selected from the group consisting of chlorobenzene, ortho-dichlorobenzene, para-dichlorobenzene, the isomers of trichlorobenzene, toluene, the isomers of xylene and mixtures thereof.

6. The process of claim 2, in which any low boilers present consist of the solvent and secondary components, where the proportion by mass of secondary components, based on the total mass of the distillation bottom stream, is not more than 0.10% by mass.

7. The process of claim 1, including step 1), wherein the pre-concentration is effected at a temperature in the range from 120° C. to 180° C. and a pressure in the range from 20 mbar$_{(abs.)}$ to 60 mbar$_{(abs.)}$.

8. The process of claim 1, in which the drying apparatus used in step 2) is selected from the group consisting of heated, product-agitating vacuum driers with a horizontal shaft, rotary tubes, disk driers, belt driers and pelletizing screws.

9. The process of claim 1, comprising:
    a) phosgenating the primary amine corresponding to the isocyanate to be prepared to obtain a liquid crude process product comprising the isocyanate to be prepared and a hydrogen chloride-comprising gaseous crude process product, with optional use of a solvent;

b) working up the liquid crude process product obtained in step a), comprising the steps of:

b.1) optionally separating dissolved phosgene and dissolved hydrogen chloride from the liquid crude process product obtained in step a) to obtain a phosgene- and hydrogen chloride-depleted liquid process product;

b.2) optionally separating solvent from the liquid crude process product obtained in step a) or from the phosgene- and hydrogen chloride-depleted liquid process product obtained in step b.1) to obtain a phosgene-, hydrogen chloride- and solvent-depleted liquid process product;

b.3) distilling the liquid crude process product obtained in step a) or the phosgene- and hydrogen chloride-depleted liquid process product obtained in step b.1) or the phosgene-, hydrogen chloride- and solvent-depleted liquid process product obtained in step b.2) to obtain a distillate stream comprising a first portion of the isocyanate to be prepared and a distillate bottom stream consisting of distillation residue, a second portion of the isocyanate to be prepared and optionally low boilers;

wherein the distillation bottom stream obtained in step b.3) is the distillation bottom stream to be worked up in step 2) or in step 1) and step 2).

10. The process of claim 9, in which the adjustment of the proportion by mass of compounds containing carbodiimide groups based on the total mass of the distillation residue supplied to the drying apparatus is brought about via exclusively one, two or all of the following measures:

A. establishing process conditions that promote the formation of compounds containing carbodiimide groups in step a) and/or in step b) and/or, if conducted, in step 1);

B. preparing compounds containing carbodiimide groups from the isocyanate to be prepared in a separate operation and supplying the compounds containing carbodiimide groups thus prepared to the drying apparatus from step 2); and C. forming compounds containing carbodiimide groups in situ in step 2).

11. The process of claim 10, including measure A, wherein measure A comprises an increase in the temperature in the respective step and/or by an increase in the residence time of the process product that passes through the respective step.

12. The process of claim 10, including measure B, wherein measure B comprises:

heating a process product containing the isocyanate to be prepared in the absence of catalysts at a temperature in the range from 200° C. to 270° C.

or in the presence of catalysts of the phospholene oxide type at a temperature in the range from 50° C. to 150° C.

13. The process of claim 11, in which step 2) is conducted at a pressure in the range from 10 $mbar_{(abs.)}$ to 250 $mbar_{(abs.)}$.

14. The process of claim 10, including measure C, wherein the drying in step 2) is conducted first in a first partial step 2.1) at a pressure in the range from >750 $mbar_{(abs.)}$ to 1013 $mbar_{(abs.)}$ and at a temperature in the range from 200° C. to 270° C. and then in a second partial step 2.2) at a pressure in the range from 10 $mbar_{(abs.)}$ to 250 $mbar_{(abs.)}$ and at a temperature in the range of 200° C. to 270° C., or at a pressure in the range from >250 $mbar_{(abs.)}$ to 750 $mbar_{(abs.)}$ and a temperature in the range from 200° C. to 270° C.

15. The process of claim 1, in which the isocyanate to be prepared is selected from the group consisting of tolylene diisocyanate, naphthyl diisocyanate, pentane 1,5-diisocyanate, hexamethylene 1,6-diisocyanate, isophorone diisocyanate, xylylene diisocyanate and diisocyanatodicyclohexylmethane.

16. The process of claim 4, in which the solvent is selected from the group consisting of chlorobenzene, ortho-dichlorobenzene, para-dichlorobenzene, the isomers of trichlorobenzene, toluene, the isomers of xylene and mixtures thereof.

17. The process of claim 4, in which any low boilers present consist of the solvent and secondary components, where the proportion by mass of secondary components, based on the total mass of the distillation bottom stream, is not more than 0.10% by mass.

18. The process of claim 12, in which step 2) is conducted at a pressure in the range from 10 $mbar_{(abs.)}$ to 250 $mbar_{(abs.)}$.

19. A process for working up a distillation bottom stream consisting of an isocyanate, optionally low boilers, and distillation residue, wherein the distillation bottom stream comes from the workup of a liquid crude process product comprising the isocyanate and is obtained by phosgenating the primary amine corresponding to the isocyanate, the working up comprising:

1) optionally pre-concentrating the distillation bottom stream in an evaporator by partially evaporating the isocyanate to be prepared which is present in the distillation bottom stream to obtain a pre-concentrated liquid stream depleted of isocyanate to be prepared; and 2) drying the distillation bottom stream or the pre-concentrated liquid stream depleted of isocyanate to be prepared which has been obtained in step 1) in a drying apparatus at a temperature in the range from 150° C. to 500° C. with evaporation and recovery of isocyanate to be prepared to form a solid process product, where the proportion by mass of compounds containing carbodiimide groups based on the total mass of the distillation residue supplied to the drying apparatus is adjusted to a value of at least 15%.

20. The process of claim 19, wherein the drying occurs at a temperature in the range from 185° C. to 300° C.

21. The process of claim 20, wherein the drying occurs at a temperature in the range from 200° C. to 270° C.

22. The process of claim 19, wherein the proportion by mass of compounds containing carbodiimide groups based on the total mass of the distillation residue supplied to the drying apparatus is adjusted to a value of at least 20%.

23. The process of claim 22, wherein the proportion by mass of compounds containing carbodiimide groups based on the total mass of the distillation residue supplied to the drying apparatus is adjusted to a value of at least 30%.

* * * * *